(12) United States Patent
Ito et al.

(10) Patent No.: US 12,127,891 B2
(45) Date of Patent: Oct. 29, 2024

(54) MEDICAL CONTROL SYSTEM AND METHOD THAT USES PACKETIZED DATA TO CONVEY MEDICAL VIDEO INFORMATION

(71) Applicant: Sony Group Corporation, Tokyo (JP)

(72) Inventors: Toshiki Ito, Kanagawa (JP); Tetsuya Mitani, Tokyo (JP); Chikako Kido, Kanagawa (JP); Keiichi Yoshioka, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 17/507,904

(22) Filed: Oct. 22, 2021

(65) Prior Publication Data

US 2022/0039905 A1   Feb. 10, 2022

Related U.S. Application Data

(63) Continuation of application No. 16/904,589, filed on Jun. 18, 2020, now Pat. No. 11,197,736, which is a
(Continued)

(30) Foreign Application Priority Data

Oct. 2, 2015   (JP) ................. 2015-196415

(51) Int. Cl.
*A61B 90/00* (2016.01)
*A61B 1/00* (2006.01)
(Continued)

(52) U.S. Cl.
CPC ............ *A61B 90/37* (2016.02); *A61B 1/0005* (2013.01); *A61B 90/00* (2016.02); *G06F 3/0481* (2013.01);
(Continued)

(58) Field of Classification Search
CPC ....... A61B 90/00; A61B 90/37; A61B 1/0005; G06F 3/0481; G06F 3/0482;
(Continued)

(56) References Cited

U.S. PATENT DOCUMENTS 5,187,579 A   2/1993  Hiyama
5,812,125 A * 9/1998  Wilkinson ............... H04N 7/15
                                               348/E7.083
(Continued)

FOREIGN PATENT DOCUMENTS

CN   1702645 A   11/2005
CN   1832548 A    9/2006
(Continued)

OTHER PUBLICATIONS

Office Action issued on Nov. 5, 2020, in corresponding European patent Application No. 16850939.6, 6 pages.
(Continued)

*Primary Examiner* — Alvin H Tan
(74) *Attorney, Agent, or Firm* — XSENSUS LLP

(57) ABSTRACT

Provided is a medical control apparatus including: a processing unit configured to cause one or both of a first display region in which an object relating to an input source of an image is to be displayed and a second display region in which an object relating to an output destination of an image is to be displayed and a third display region in which an object for controlling the input source or the output destination is to be displayed, to be displayed in one screen.

24 Claims, 19 Drawing Sheets

Related U.S. Application Data continuation of application No. 15/761,325, filed as application No. PCT/JP2016/073901 on Aug. 16, 2016, now abandoned.

(51) Int. Cl.

| | | |
|---|---|---|
| *G06F 3/0481* | (2022.01) | |
| *G06F 3/0482* | (2013.01) | |
| *G09G 5/14* | (2006.01) | |
| *G16H 30/20* | (2018.01) | |
| *G16H 40/63* | (2018.01) | |
| *H04N 21/431* | (2011.01) | |
| *H04N 21/436* | (2011.01) | |
| *G06F 3/0483* | (2013.01) | |

(52) U.S. Cl.
CPC ............. *G06F 3/0482* (2013.01); *G09G 5/14* (2013.01); *G16H 30/20* (2018.01); *G16H 40/63* (2018.01); *H04N 21/431* (2013.01); *H04N 21/436* (2013.01); *G06F 3/0483* (2013.01); *G06F 2203/04803* (2013.01); *G09G 2354/00* (2013.01); *G09G 2380/08* (2013.01)

(58) Field of Classification Search
CPC ........ G06F 3/0483; G06F 2203/04803; G09G 5/14; G09G 2354/00; G09G 2380/08; G16H 30/20; G16H 40/63; H04N 21/431; H04N 21/436
See application file for complete search history.

(56) References Cited

U.S. PATENT DOCUMENTS

| | | | |
|---|---|---|---|
| 6,493,036 | B1 | 12/2002 | Fernandez |
| 7,312,764 | B2 | 12/2007 | Driver et al. |
| 8,069,420 | B2 | 11/2011 | Plummer |
| 8,533,752 | B2 | 9/2013 | Lee et al. |
| 8,884,886 | B2 | 11/2014 | Bonczek et al. |
| 9,241,062 | B2 * | 1/2016 | Khalid ............... G06F 9/452 |
| 9,363,573 | B2 | 6/2016 | Kumar |
| 9,642,606 | B2 | 5/2017 | Charles et al. |
| 9,715,506 | B2 * | 7/2017 | Rosen ............. G06F 16/285 |
| 10,445,465 | B2 | 10/2019 | Vaidya et al. |
| 10,694,933 | B2 | 6/2020 | Yamaguchi |
| 10,714,219 | B2 | 7/2020 | Altobello et al. |
| 2004/0255329 | A1 | 12/2004 | Compton et al. |
| 2006/0025679 | A1 | 2/2006 | Viswanathan |
| 2006/0064716 | A1 | 3/2006 | Sull et al. |
| 2006/0152516 | A1 | 7/2006 | Plummer |
| 2007/0120550 | A1 | 5/2007 | Miyake et al. |
| 2008/0033450 | A1 | 2/2008 | Bayer et al. |
| 2008/0055239 | A1 | 3/2008 | Garibaldi et al. |
| 2008/0122924 | A1 | 5/2008 | Tashiro |
| 2009/0217165 | A1 | 8/2009 | Ito et al. |
| 2009/0271738 | A1 | 10/2009 | Glaser-Seidnitzer et al. |
| 2009/0282437 | A1 * | 11/2009 | Malec ............... G06F 3/1423 725/40 |
| 2010/0302156 | A1 | 12/2010 | Arthur |
| 2012/0173281 | A1 | 7/2012 | Dilella et al. |
| 2012/0182244 | A1 | 7/2012 | Arthur |
| 2012/0189173 | A1 | 7/2012 | Markowitz et al. |
| 2012/0226771 | A1 | 9/2012 | Harrington et al. |
| 2012/0254933 | A1 | 10/2012 | Lee |
| 2012/0265084 | A1 | 10/2012 | Stewart et al. |
| 2013/0197357 | A1 | 8/2013 | Green et al. |
| 2013/0243282 | A1 | 9/2013 | Sato et al. |
| 2015/0061972 | A1 | 3/2015 | Seo et al. |
| 2015/0138329 | A1 | 5/2015 | Braun et al. |
| 2015/0269315 | A1 | 9/2015 | Arakita et al. |
| 2015/0332196 | A1 | 11/2015 | Stiller et al. |
| 2016/0000307 | A1 | 1/2016 | Akimoto et al. |
| 2016/0092637 | A1 | 3/2016 | Kudo et al. |
| 2016/0103960 | A1 | 4/2016 | Hume et al. |
| 2016/0125635 | A1 | 5/2016 | Nam et al. |
| 2016/0378939 | A1 | 12/2016 | Baumberger et al. |
| 2018/0015218 | A1 | 1/2018 | Welsch |
| 2018/0271613 | A1 | 9/2018 | Ito et al. |
| 2019/0261043 | A1 | 8/2019 | Sato et al. |

FOREIGN PATENT DOCUMENTS

| | | | |
|---|---|---|---|
| CN | 103099676 | A | 5/2013 |
| CN | 103142309 | A | 6/2013 |
| CN | 103153171 | A | 6/2013 |
| CN | 103177183 | A | 6/2013 |
| CN | 103845071 | A | 6/2014 |
| CN | 104105442 | A | 10/2014 |
| CN | 1105050479 | A | 11/2015 |
| EP | 1870827 | A1 | 12/2007 |
| EP | 2843919 | A1 | 3/2015 |
| EP | 2957216 | A1 | 12/2015 |
| ES | 2342429 | T3 | 7/2010 |
| JP | 3012342 | B2 | 2/2000 |
| JP | 2001-000449 | A | 1/2001 |
| JP | 2002-125219 | A | 4/2002 |
| JP | 2004-313341 | A | 11/2004 |
| JP | 2005110877 | A | 4/2005 |
| JP | 2005-245961 | A | 9/2005 |
| JP | 2005-304935 | A | 11/2005 |
| JP | 2006-255395 | A | 9/2006 |
| JP | 2006-288955 | A | 10/2006 |
| JP | 2008-000282 | A | 1/2008 |
| JP | 2008086665 | A | 4/2008 |
| JP | 5034256 | B2 | 9/2012 |
| JP | 2014104099 | A | 6/2014 |
| JP | 5771757 | B2 | 9/2015 |
| KR | 10-2015-0026367 | A | 3/2015 |
| WO | 2005/102142 | A1 | 11/2005 |
| WO | 2013/111684 | A1 | 8/2013 |
| WO | 2014/168128 | A1 | 10/2014 |

OTHER PUBLICATIONS

Ciarlone, "10 Gigabit Ethernet Switches: 6 Benefits You Might Not Have Considered," Apr. 9, 2015, Available https://info.hummingbirdnetworks.com/blog/10-gigabit-ethernet-switches-6-benefits (Year: 2015).

Customcable.Ca, "Wired vs. Wireless Connections," Dec. 11, 2011, Available https://customcable.ca/wired-vs-wireless/ (Year:2011).

Borida, "Decide Between VGA, DVI, and HDMI for Your Monitor Connection," May 18, 2010, Available https://www.pcworld.com/article/196618/Decide_Between_VGA_DVI_and_HDMI_for_Your_Monitor_Connection.html (Year: 2010).

Mueller, "Two in One—Understanding Dual-Core Processors," May 16, 2005, Available https://www.informit.com/articles/article.aspx?p=404293&seqNum=4 (Year: 2005).

Extended European Search Report of EP Patent Application No. 16850939.6, issued on Dec. 7, 2018, 11 pages.

International Search Report and Written Opinion of PCT Application No. PCT/JP2016/073901, issued on Nov. 1, 2016, 11 pages.

* cited by examiner

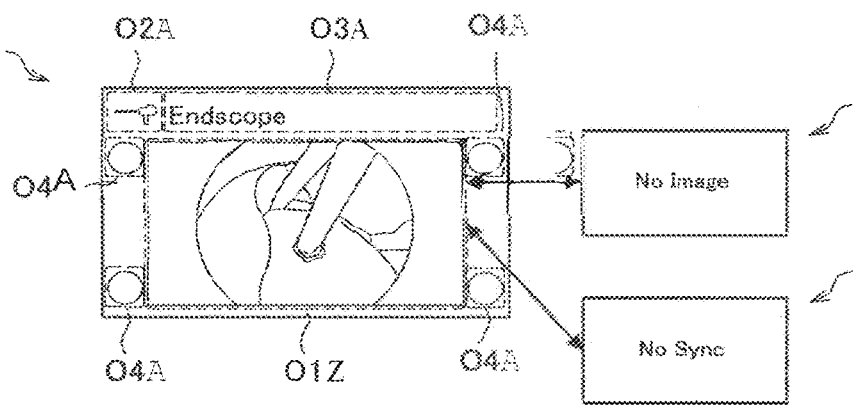
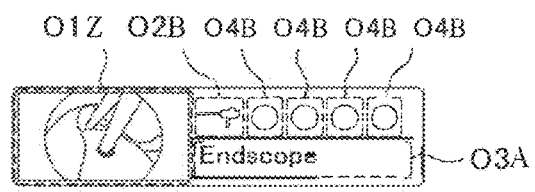
FIG. 6
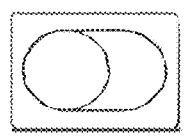
FIG. 7A — WHEN TURNED OFF
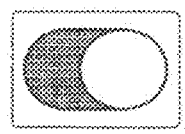
FIG. 7B — WHEN TURNED ON

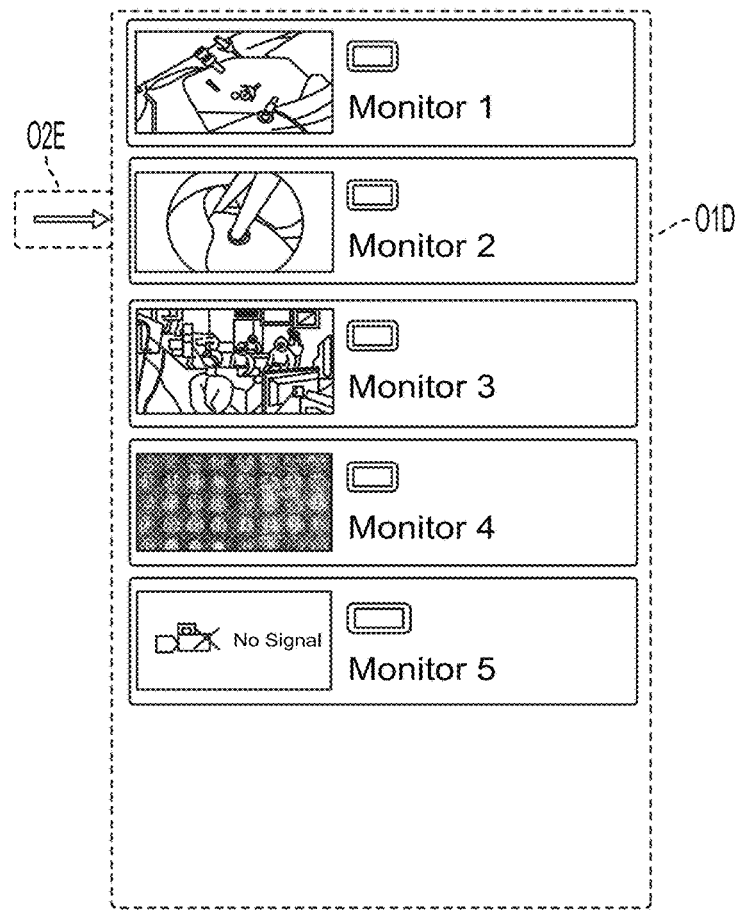
FIG. 14
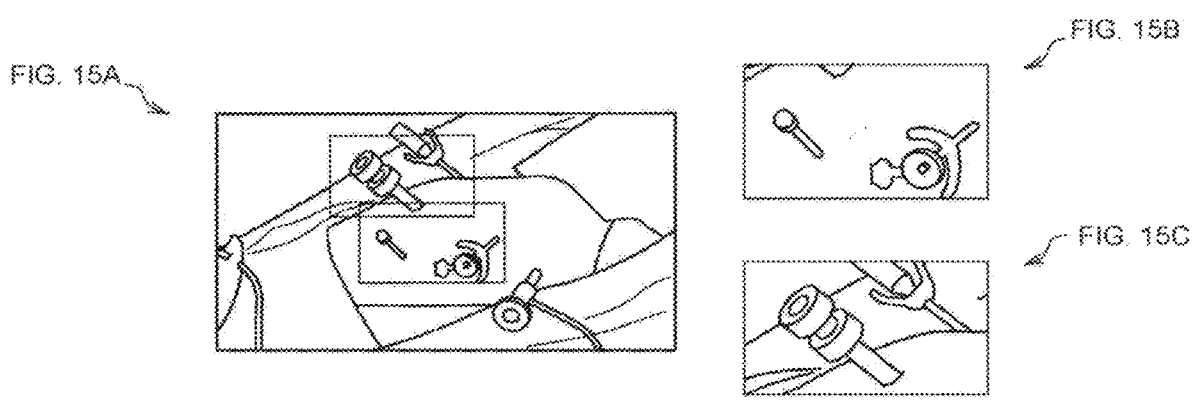

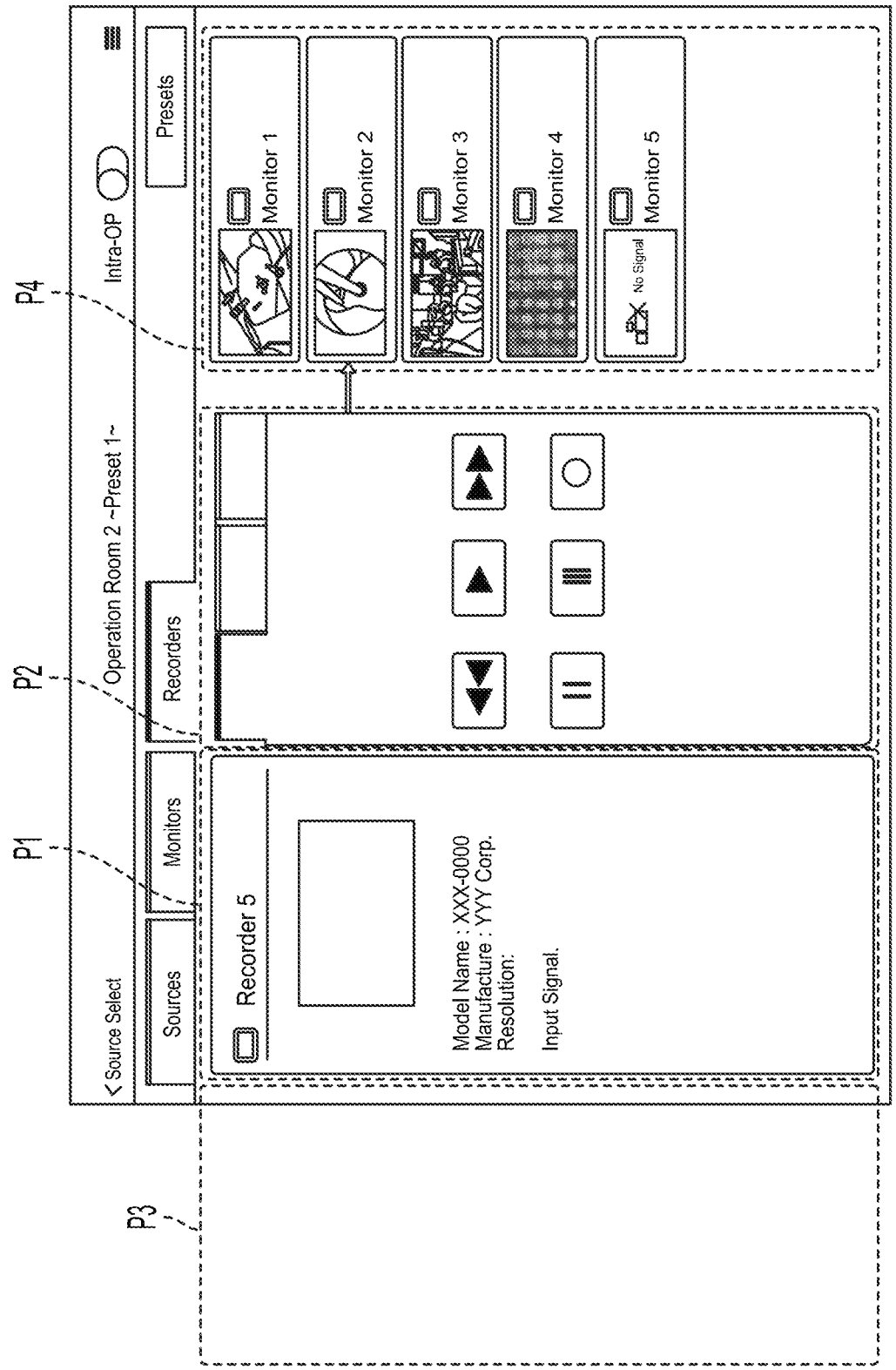

MEDICAL CONTROL SYSTEM AND METHOD THAT USES PACKETIZED DATA TO CONVEY MEDICAL VIDEO INFORMATION

CROSS-REFERENCE TO RELATED APPLICATIONS

The present application is a continuation of U.S. application Ser. No. 16/904,589, filed Jun. 18, 2020, which is a continuation of U.S. application Ser. No. 15/761,325, filed Mar. 19, 2018 (now Abandoned), which is a U.S. National Phase of International Patent Application No. PCT/JP2016/073901 filed on Aug. 16, 2016, which claims priority benefit of Japanese Patent Application No. JP 2015-196415, filed in the Japan Patent Office on Oct. 2, 2015. Each of the above-referenced applications are hereby incorporated herein by reference in its entirety.

TECHNICAL FIELD

The present disclosure relates to a medical control apparatus, a control method, a program, and a medical control system.

BACKGROUND ART

A technology relating to a medical control system in which a plurality of apparatuses are connected through communication has been developed. Examples of the technology relating to the medical control system can include, for example, a technology disclosed in the following Patent Literature 1 and a technology disclosed in the following Patent Literature 2.

CITATION LIST

Patent Literature

Patent Literature 1: JP 2001-000449A
Patent Literature 2: JP 2006-000536A

DISCLOSURE OF INVENTION

Technical Problem

A medical control system includes, for example, a medical control apparatus such as an operating room (OR) controller for controlling input/output of an image (a still image or a moving image). Here, a typical existing medical control apparatus causes, for example, an "apparatus which becomes a signal source of an image signal, such as medical equipment having an imaging function such as an endoscope, and an imaging device provided in an operating room" constituting the medical control system and an "apparatus which becomes an output destination of an image, such as display device which can display an image" constituting the medical control system, to be displayed in one screen. The existing medical control apparatus then, for example, switches between input and output of an image on the basis of manipulation by a user of the medical control system, such as a healthcare professional (hereinafter, simply referred to as a "user"). In the following description, there is a case where the apparatus which becomes a signal source of an image signal will be referred to as an "input source". Further, in the following description, there is a case where the apparatus which becomes an output destination of an image will be referred to as an "output destination".

As described above, by the medical control apparatus causing the input source and the output destination constituting the medical control system to be displayed in one screen, browsability of the input source and the output destination is improved. Therefore, as described above, by the medical control apparatus causing the input source and the output destination constituting the medical control system to be displayed in one screen, there is a possibility that visibility of the input source and the output destination may be improved.

However, in the case where the existing medical control apparatus as described above is used, control associated with input/output of an image and control of an apparatus (the input source or the output destination) constituting the medical control system cannot be performed in one screen.

The present disclosure proposes new and improved medical control apparatus, control method, program and medical control system which can improve operability of the user.

Solution to Problem

According to the present disclosure, there is provided a medical control apparatus including: a processing unit configured to cause one or both of a first display region in which an object relating to an input source of an image is to be displayed and a second display region in which an object relating to an output destination of an image is to be displayed and a third display region in which an object for controlling the input source or the output destination is to be displayed, to be displayed in one screen.

Further, according to the present disclosure, there is provided a control method to be executed by a medical control apparatus, the method including: a step of causing one or both of a first display region in which an object relating to an input source of an image is to be displayed and a second display region in which an object relating to an output destination of an image is to be displayed, and a third display region in which an object for controlling the input source or the output destination is to be displayed, to be displayed in one screen.

Further, according to the present disclosure, there is provided a program for causing a computer to implement a function of causing one or both of a first display region in which an object relating to an input source of an image is to be displayed and a second display region in which an object relating to an output destination of an image is to be displayed, and a third display region in which an object for controlling the input source or the output destination is to be displayed, to be displayed in one screen.

Further, according to the present disclosure, there is provided a medical control system including: an apparatus which serves as an input source of an image; an apparatus which serves as an output destination of an image; and a medical control apparatus, in which the medical control apparatus includes a processing unit configured to cause one or both of a first display region in which an object relating to the input source is to be displayed and a second display region in which an object relating to the output destination is to be displayed, and a third display region in which an object for controlling the input source or the output destination is to be displayed, to be displayed in one screen.

Advantageous Effects of Invention

According to the present disclosure, it is possible to improve operability of the user.

Note that the effects described above are not necessarily limitative. With or in the place of the above effects, there may be achieved any one of the effects described in this specification or other effects that may be grasped from this specification.

BRIEF DESCRIPTION OF DRAWINGS

FIGS. 5A, 5B, and 5C are explanatory diagrams for explaining an example of display at the medical control system to which a control method according to the present embodiment is applied.

FIG. 6 is an explanatory diagram for explaining an example of display at the medical control system to which a control method according to the present embodiment is applied.

FIGS. 7A and 7B are explanatory diagrams for explaining an example of display at the medical control system to which a control method according to the present embodiment is applied.

FIG. 14 is an explanatory diagram for explaining an example of display at the medical control system to which a control method according to the present embodiment is applied.

FIGS. 15A, 15B, and 15C are explanatory diagrams for explaining an example of display at the medical control system to which a control method according to the present embodiment is applied.

FIG. 19B is an explanatory diagram for explaining an example of display at the medical control system to which a control method according to the present embodiment is applied.

MODE(S) FOR CARRYING OUT THE INVENTION

Figure 1:
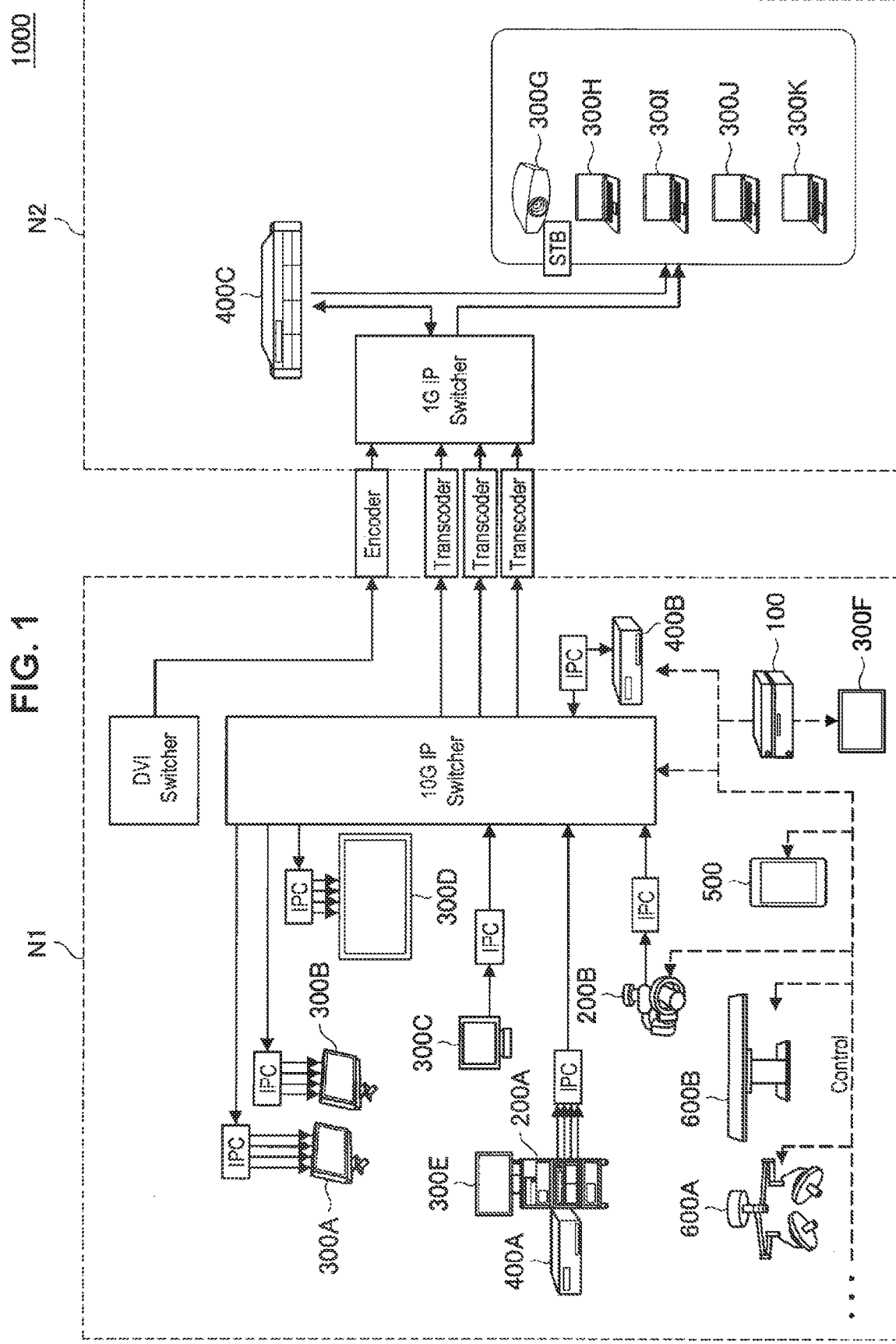
FIG. 1 is an explanatory diagram illustrating an example of a medical control system according to the present embodiment.

Hereinafter, a preferred embodiment of the present disclosure will be described in detail with reference to the appended drawings. Note that, in this specification and the appended drawings, structural elements that have substantially the same function and structure are denoted with the same reference numerals, and repeated explanation of these structural elements is omitted.

Further, in the following description, description will be provided in the following order.
1. Control method according to present embodiment
2. Medical control apparatus according to present embodiment
3. Program according to present embodiment
(Control Method According to Present Embodiment)

First, a control method according to the present embodiment will be described. In the following description, an example will be described where a medical control apparatus according to the present embodiment performs processing associated with the control method according to the present embodiment.

[1] Processing Associated with Control Method According to Present Embodiment

As described above, in the case where an existing medical control apparatus is used, control associated with input/output of an image and control of an apparatus (an input source or an output destination) constituting the medical control system cannot be performed in one screen.

Therefore, the medical control apparatus according to the present embodiment enables control associated with input/output of an image and control of an input source or an output destination constituting the medical control system to be performed in one screen.

Here, examples of the input source according to the present embodiment can include, for example, an arbitrary apparatus which can become a signal source of an image signal, such as medical equipment having an imaging function such as an endoscope, an imaging device provided in an operating room, and an apparatus having a function of reproducing image data stored in a recording medium.

Further, examples of the output destination according to the present embodiment can include, for example, an arbitrary apparatus which can become an output destination of an image, such as a display device which can display an image and an apparatus having a function of recording an image in a recording medium.

More specifically, the medical control apparatus according to the present embodiment causes a plurality of display regions to be displayed in one screen, for example, as described in display examples of the following (1) to (3) (control processing).

Examples of the display screen according to the present embodiment in which a plurality of display regions are to be displayed can include, for example, a display screen of a display device provided at an arbitrary apparatus (or a display device connected to an arbitrary apparatus), such as a tablet type apparatus, a computer such as a personal computer (PC) and a communication apparatus such as a smartphone. Further, the display device constituting the display screen according to the present embodiment may be a device such as, for example, a touch panel, which can perform display and allows user manipulation.

The medical control apparatus according to the present embodiment causes a plurality of display regions to be displayed in one screen by, for example, causing control data including a command for causing display to be performed and display data to be transmitted to an apparatus at which the plurality of display regions are to be displayed in one screen (hereinafter, there is a case where the apparatus will be referred to as a "display target apparatus"). The medical control apparatus according to the present embodiment, for example, causes a communication unit (which will be described later) provided at the medical control apparatus according to the present embodiment or an external communication device connected to the medical control apparatus according to the present embodiment to transmit the control data.

By performing the control processing as described above, the medical control apparatus according to the present embodiment enables control associated with input/output of an image and control of an input source or an output destination constituting the medical control system to be performed in one screen.

Here, examples of the display regions to be displayed in one screen according to the present embodiment can include, for example, the following first display region, second display region and third display region.

First display region: a display region in which objects relating to an input source of an image are to be displayed Second display reg10n: a display reg10n m which objects relating to an output destination of an image are to be displayed Third display region: a display region in which objects for controlling an input source or an output destination are to be displayed Further, examples of the object according to the present embodiment can include an arbitrary display object which can be displayed on the display screen, such as, for example, a "thumbnail image corresponding to an image output from an input source or an image input to an output destination", a "character string" and an "operation object such as a button and a slide bar, which can be manipulated by a user". Specific examples of the object according to the present embodiment will be described in an example of display in the medical control system which will be described later.

Here, examples of the thumbnail image according to the present embodiment can include a still image and a moving image. Further, the thumbnail image according to the present embodiment may be regularly updated, for example, every 1 [FPS] or may be irregularly updated. By the thumbnail image being updated, an image most recently output from the input source or an image most recently input to the output destination can be reflected in the thumbnail image.

(1) First Example of Display in One Screen Through Control Processing

The medical control apparatus according to the present embodiment causes the first display region, the second display region and the third display region to be displayed in one screen.

In the case where display according to a first example is performed, the medical control apparatus according to the present embodiment causes the following objects to be respectively displayed in the first display region, the second display region and the third display region.

First display region: objects relating to the input source

Second display region: objects relating to the output destination at which an image of the input source can be displayed Third display region: objects for controlling the input source Specific examples of the display according to the first example can include, for example, a Sources screen on a device control screen which will be described later. Note that it goes without saying that the "specific examples of the display according to the first example" and "examples of objects to be respectively displayed in the first display region, the second display region and the third display region" are not limited to the above-described examples.

(2) Second Example of Display in One Screen Through Control Processing

The medical control apparatus according to the present embodiment causes the first display region and the third display region to be displayed in one screen.

In the case where display according to the second example is performed, the medical control apparatus according to the present embodiment causes, for example, the following objects to be respectively displayed in the first display region and the third display region.

First display region: objects relating to the input source which can cause the output destination to perform display or objects relating to the input source which can cause the output destination to record an image Third display region: objects for controlling the output destination Specific examples of the display according to the second example can include, for example, a Monitors screen in the device control screen which will be described later and a Recorders screen in the device control screen which will be described later. Note that, it goes without saying that the "specific examples of the display according to the second example" and the "examples of the objects to be respectively displayed in the first display region and the third display region" are not limited to the above-described examples.

(3) Third Example of Display in One Screen Through Control Processing

The medical control apparatus according to the present embodiment causes the second display region and the third display region to be displayed in one screen.

In the case where display according to the third example is performed, the medical control apparatus according to the present embodiment causes, for example, the following objects to be respectively displayed in the second display region and the third display region.

Second display region: objects relating to the output destination at which an image of the input source can be displayed Third display region: objects for controlling the input source.

Specific examples of the display according to the third example can include, for example, a Recorders screen in the device control screen which will be described later. Note that, it goes without saying that the "specific examples of the display according to the third example" and the "examples of the objects to be respectively displayed in the second display region and the third display region" are not limited to the above-described examples.

The medical control apparatus according to the present embodiment causes one or both of the first display region and the second display region, and the third display region to be displayed in one screen as described in, for example, the first example of the display described in the above (1) to the third example of the display described in the above (3) by performing the control processing associated with the control method according to the present embodiment.

Here, the first display region is a display region in which objects relating to the input source are to be displayed, and the second display region is a display region in which objects relating to the output destination are to be displayed. Further, the third display region is a display region in which objects for controlling the input source or the output destination are to be displayed.

Therefore, by the control processing being performed, it is possible to cause, for example, "control associated with input/output of an image signal to/from the input source or the output destination existing inside or outside an operating room and control of the input source or the output destination to be performed in one screen". Further, as a result of the "control associated with input/output of an image signal to/from the input source or the output destination existing inside or outside an operating room and control of the input source or the output destination being able to be performed in one screen", the user can more efficiently perform control associated with input/output an image signal to/from the input source or the output destination and control the input source or the output destination.

Therefore, by the medical control apparatus according to the present embodiment performing the control processing associated with the control method according to the present embodiment, it is possible to realize improvement of operability of the user.

Note that the above-described control processing is processing divided from the processing associated with the control method according to the present embodiment for convenience sake. Therefore, in the processing associated with the control method according to the present embodiment, the above-described control processing can be regarded as, for example, two or more types of processing (depending on an arbitrary way of dividing the processing).

[2] Example of Display in Medical Control System to which Control Method According to Present Embodiment is Applied The control processing associated with the control method according to the present embodiment will be described next using an example of display in the medical control system to which the control method according to the present embodiment is applied.

FIG. 1 is an explanatory diagram illustrating an example of the medical control system 1000 according to the present embodiment.

FIG. 1 illustrates an example of a system in which an image signal which is made to conform to IP is transmitted among apparatuses via an internet protocol converter (IPC), a switcher, an encoder, a transcoder, or the like. In FIG. 1, for example, a "10G IP Switcher", a "DVI Switcher" and a "1G IP Switcher" correspond to the switchers. Further, in FIG. 1, for example, an "Encoder" corresponds to the encoder, and, for example, a "Transcoder" corresponds to the transcoder. Note that, in the medical control system according to the present embodiment, it is also possible to employ a configuration where an image signal which is made to conform to IP is not transmitted.

Further, FIG. 1 illustrates an example where the medical control system 1000 includes a network N1 inside the operating room and a network N2 outside the operating room. Note that the medical control system 1000 may include, for example, only the network N1 inside the operating room.

The medical control system 1000 includes, for example, a medical control apparatus 100, input source apparatuses 200A, 200B, . . . , output destination apparatuses 300A, 300B, . . . , apparatuses 400A, 400B, . . . , having functions of one or both of the input source and the output destination, a display target apparatus 500 at which various kinds of control screens are to be displayed, and other apparatuses 600A, 600B, . . . , controlled by the medical control apparatus 100. The respective apparatuses are connected, for example, through wired communication of an arbitrary communication scheme or through wireless communication of an arbitrary communication scheme via an apparatus such as the IPC and the switcher.

Examples of the input source apparatuses 200A, 200B, . . . , can include medical equipment having an imaging function such as an endoscope (for example, the input source apparatus 200A) and an imaging device provided in the operating room, or the like, (for example, the input source apparatus 200B), for example, as illustrated in FIG. 1. In the following description, there is a case where the input source apparatuses 200A, 200B, . . . , will be collectively referred to as an "input source apparatus 200" or one of the input source apparatuses 200A, 200B, . . . , will be referred to as the "input source apparatus 200".

Examples of the output destination apparatuses 300A, 300B, . . . , can include, for example, a display device which can display an image. Examples of the display device can include, for example, a monitor provided in the operating room (for example, the output destination apparatuses 300A to 300F), an image projection apparatus such as a projector (for example, the output destination apparatus 300G), a monitor provided at the PC, or the like, (for example, the output destination apparatuses 300H to 300K) as illustrated in FIG. 1. In the following description, there is a case where the output destination apparatuses 300A, 300B, . . . , will be collectively referred to as an "output destination apparatus 300" or one of the output destination apparatuses 300A, 300B, . . . , will be referred to as the "output destination apparatus 300".

Examples of the apparatuses 400A, 400B, . . . , having functions of one or both of the input source and the output destination can include an apparatus having functions of one or both of a function of recording an image in a recording medium and a function of reproducing image data stored in the recording medium. Specifically, examples of the apparatuses 400A, 400B, . . . , having functions of one or both of the input source and the output destination can include a recorder (for example, the apparatuses 400A and 400B) and a server (for example, the apparatus 400C), for example, as illustrated in FIG. 1. In the following description, there is a case where the apparatuses 400A, 400B, . . . , having functions of one or both of the input source and the output destination will be collectively referred to as an "apparatus 400" or one of the apparatuses 400A, 400B, . . . , having functions of one or both of the input source and the output destination will be referred to as the "apparatus 400". Further, in the following description, an example where the apparatus 400 is a recorder will be mainly described.

Examples of the display target apparatus 500 can include, for example, an arbitrary apparatus such as a tablet type apparatus, a computer such as a PC, a communication apparatus such as a smartphone. In FIG. 1, a tablet type apparatus including a touch panel is illustrated as the display target apparatus 500. Note that the medical control system 1000 may include a plurality of display target apparatuses. Further, in the medical control system 1000, for example, one of the medical control apparatus 100, the input source apparatus 200, the output destination apparatus 300 and the apparatus 400 may play a role of the display target apparatus.

Examples of other apparatuses 600A, 600B, . . . , can include a lighting apparatus at an operating table (other apparatus 600A), the operating table (other apparatus 600B), or the like, for example, as illustrated in FIG. 1. Note that the medical control apparatus 100 does not have to have a function of controlling the other apparatuses 600A, 600B, . . . .

(I) A device selection screen and (II) a device control screen will be described below as an example of display to be displayed on a display screen of the display target apparatus 500 in the medical control system 1000 as illustrated in FIG. 1.

(I) Device Selection Screen

FIG. 2 to FIG. 9 are explanatory diagrams for explaining an example of display in the medical control system 1000 to which the control method according to the present embodiment is applied. FIG. 2 to FIG. 9 each illustrates the whole device selection screen or part of the device selection screen to be displayed on the display screen of the display target apparatus 500. The device selection screen will be described below while referring to FIG. 2 to FIG. 9 as appropriate.

Figure 2:
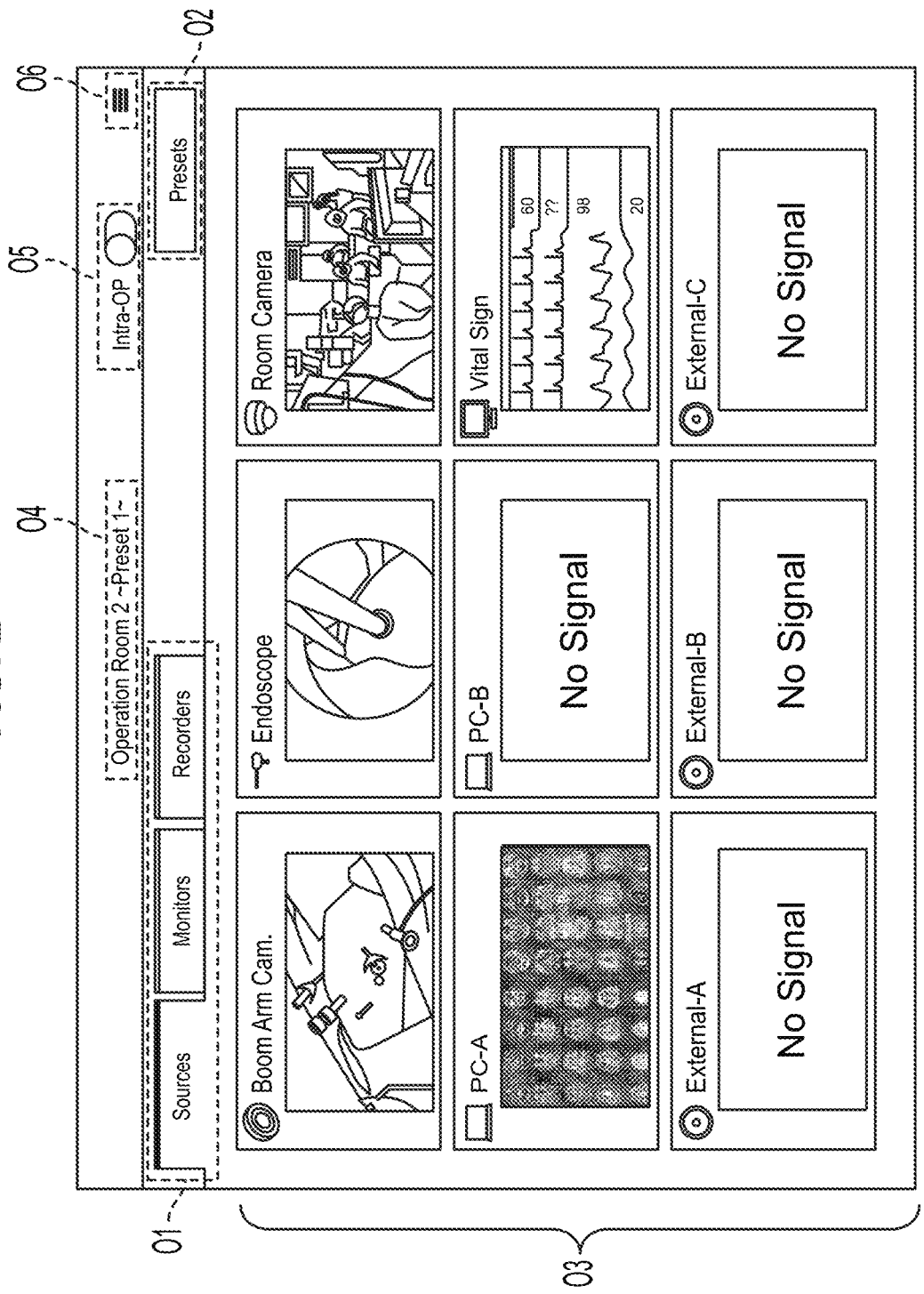
FIG. 2 is an explanatory diagram for explaining an example of display at the medical control system to which a control method according to the present embodiment is applied.

FIG. 2 illustrates an example of the device selection screen. Referring to FIG. 2, the device selection screen includes, for example, a device category selection tab (O1 illustrated in FIG. 2), a preset button (O2 illustrated in FIG. 2), a device selection button (O3 illustrated in FIG. 2), location name display (O4 illustrated in FIG. 2), an Intra-OP switch (O5 illustrated in FIG. 2), and a context menu button (O6 illustrated in FIG. 2).

The device category selection tab (O1 illustrated in FIG. 2) is a tab for switching a category of a device which can be displayed on a display screen. In FIG. 2, as the category of the device which can be displayed on the display screen, "Sources" corresponding to the input source apparatus 200, "Monitors" corresponding to the output destination apparatus 300 and "Recorders" corresponding to the apparatus 400 are illustrated. Here, FIG. 2 illustrates a case where "Sources" is selected in the device category selection tab.

The preset button (O2 illustrated in FIG. 2) is a button for making the screen transition to a screen set in advance. Here, the preset button may be highlighted, for example, by being colored, by being blinked, or the like.

The device selection button (O3 illustrated in FIG. 2) is a button for selecting a device, and by the device selection button being manipulated, the screen transitions to the device control screen which will be described later. Because, in FIG. 2, "Sources" is selected in the device category selection tab, by the device selection button being manipulated, the screen transitions to a Sources screen in the device control screen which will be described later.

Figure 3:
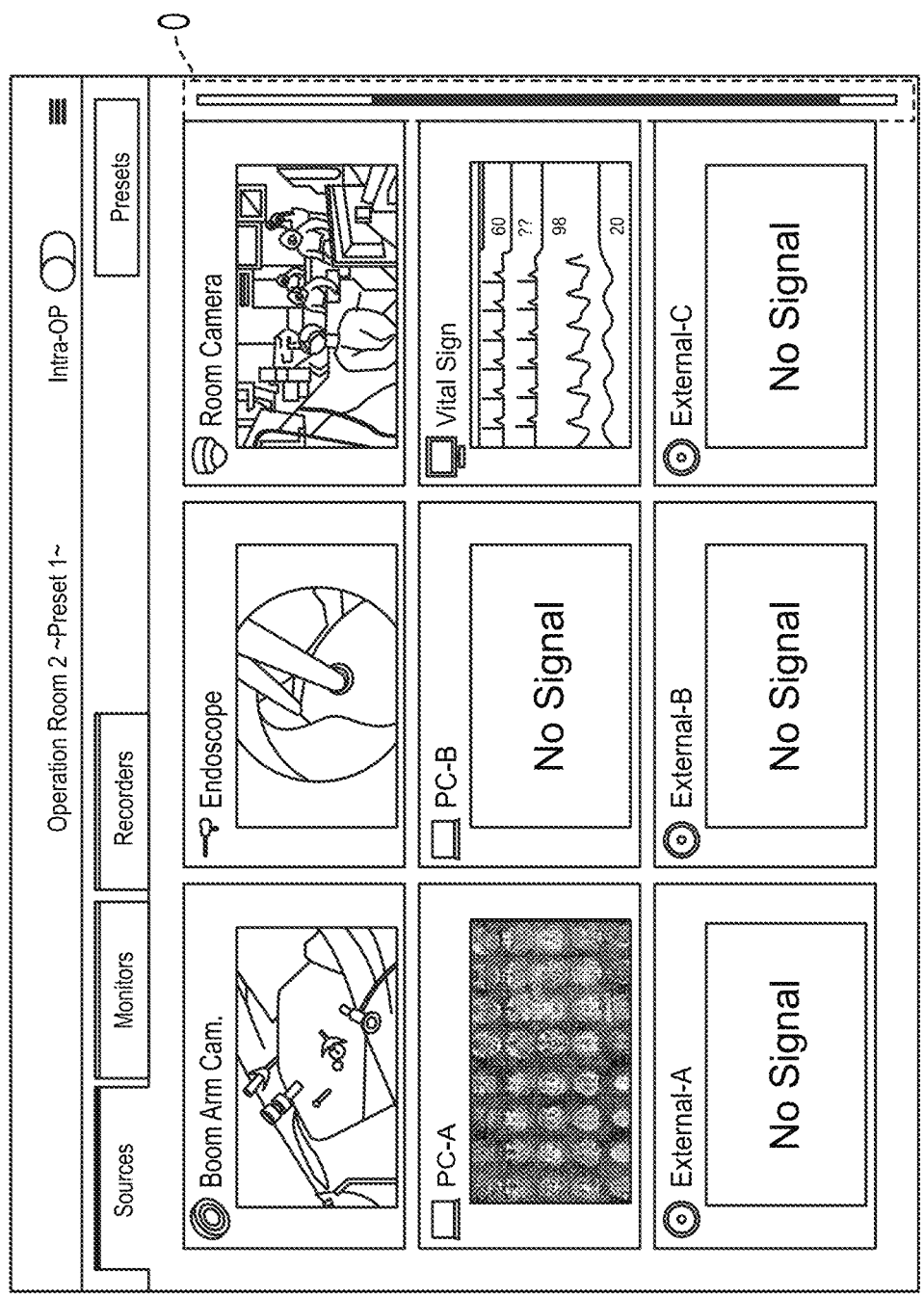
FIG. 3 is an explanatory diagram for explaining an example of display at the medical control system to which a control method according to the present embodiment is applied.

Here, in the case where there are too many device selection buttons to be displayed within one screen when each of the device selection buttons is displayed at a size illustrated in FIG. 2, a scroll bar is displayed, for example, as indicated with O in FIG. 3.

Figure 4:
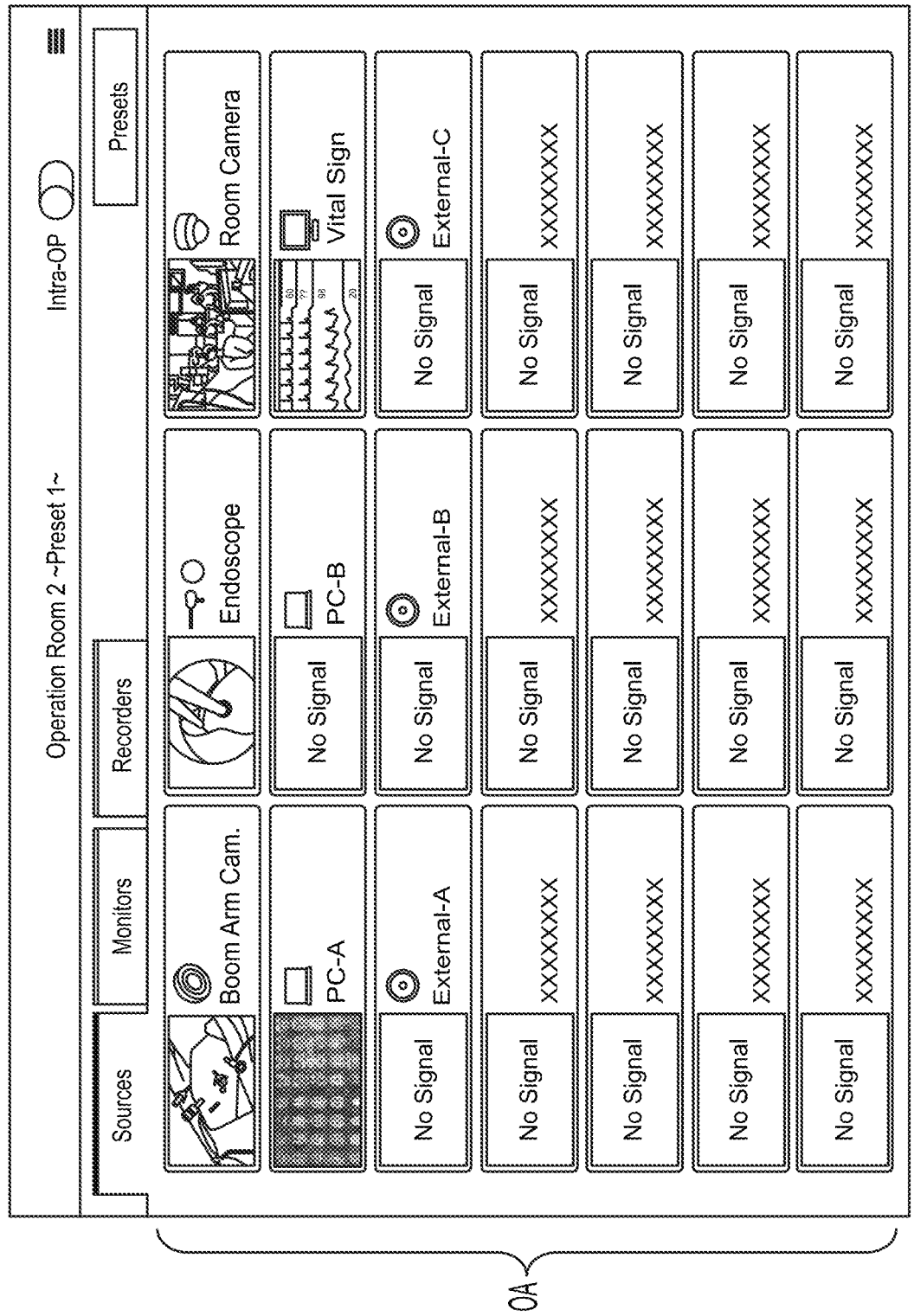
FIG. 4 is an explanatory diagram for explaining an example of display at the medical control system to which a control method according to the present embodiment is applied.

Further, in the case where there are too many device selection buttons to be displayed within one screen when each of the device selection buttons is displayed at a size illustrated in FIG. 2, each of the device selection buttons may be displayed at a smaller size, for example, as illustrated in FIG. 4.

FIGS. 5A, 5B, and 5C illustrate an example of a configuration of the device selection button, and illustrates an example of the device selection button displayed in the device selection screen illustrated in FIG. 2.

The device selection button displayed in the device selection screen illustrated in FIG. 2 includes, for example, a thumbnail image (O1Z illustrated in FIG. 5A), an icon (O2A illustrated in FIG. 5A), device name display (O3A illustrated in FIG. 5A,) and status display (O4A illustrated in FIG. 5A) as illustrated in FIG. 5A.

The thumbnail image (O1Z illustrated in FIG. 5A) illustrated in FIG. 5A indicates an image output by a device which is an input source.

Here, while examples of the thumbnail image can include a still image, the thumbnail image may be a moving image. As described above, the thumbnail image according to the present embodiment can be regularly or irregularly updated. In the case where the thumbnail image is updated, it is possible to reflect an image most recently output from the input source in the thumbnail image.

Further, for example, in the case where a parameter of a device which is an input source is adjusted, or the like, in the device control screen which will be described later, the image output from the input source after the parameter is adjusted is reflected in the thumbnail image.

As an example, in the case where a parameter associated with zoom of the device which is the input source is adjusted in the device control screen which will be described later, the zoomed image is reflected in the thumbnail image.

Further, in the case where the thumbnail image cannot be acquired, display as illustrated FIG. 5B or FIG. 5C is performed in accordance with the following states.

In the case where a thumbnail has not been acquired yet: FIG. 5B

In the case where there is no input yet: FIG. 5C

The icon (O2A illustrated in FIG. 5A) is an icon indicating a type of the device.

The device name display (O3A in FIG. 5A) indicates name of the device. A region of the device name display (O3A in FIG. 5A) is set so as to stretch over the width of the device selection button so that, for example, long device name can be displayed.

The status display (O4A illustrated in FIG. 5A) indicates a state of the device with simple display like an icon. The status display is displayed at four corners, for example, as illustrated in FIG. 5A. Further, in the case where the status display is displayed at four corners, up to four types of status display can be displayed.

FIG. 6 illustrates another example of the configuration of the device selection button and illustrates an example of a configuration of the device selection button displayed in the device selection screen illustrated in FIG. 4.

The device selection button displayed in the device selection screen (OA) illustrated in FIG. 4 includes a thumbnail image (O1Z illustrated in FIG. 6), an icon (O2B illustrated in FIG. 6), device name display (O3A illustrated in FIG. 6) and status display (O4B illustrated in FIG. 6), for example, in a similar manner to the device selection button illustrated in FIG. 4, as illustrated in FIG. 6.

Referring to FIG. 2 again, an example of the device selection screen will be described. The location name display (O4 illustrated in FIG. 2) indicates a location such as operating room name which is currently being selected.

The Intra-OP switch (O5 illustrated in FIG. 2) is a switch for switching between a state where an operation is being performed and a state where an operation is not being performed. Here, in the case where the Intra-OP switch is put into an ON state which indicates that an operation is being performed, user manipulation set in advance and editing of various kinds of data are restricted in the device selection screen and the device control screen which will be described later.

FIGS. 7A and 7B illustrate an example of a state of the Intra-OP switch. In the case where the Intra-OP switch is put into an OFF state which does not indicate that an operation is being performed, the Intra-OP switch is, for example, put into a state as illustrated in FIG. 7A. Further, in the case where the Intra-OP switch is put into an ON state which indicates that an operation is being performed, the Intra-OP switch is, for example, put into a state as illustrated in FIG. 7B, and is more highlighted than in a case of the OFF state.

As illustrated in FIG. 7B, by highlighting the Intra-OP switch more in a case of the ON state than the Intra-OP switch in a case of the OFF state, it is, for example, possible to allow the user to recognize that the state is a state indicating that an operation is being performed.

Referring to FIG. 2 again, an example of the device selection screen will be described. The context menu button (O6 illustrated in FIG. 2) is a menu button for allowing the user to perform detailed manipulation, editing of various kinds of data, or the like.

Figure 8:
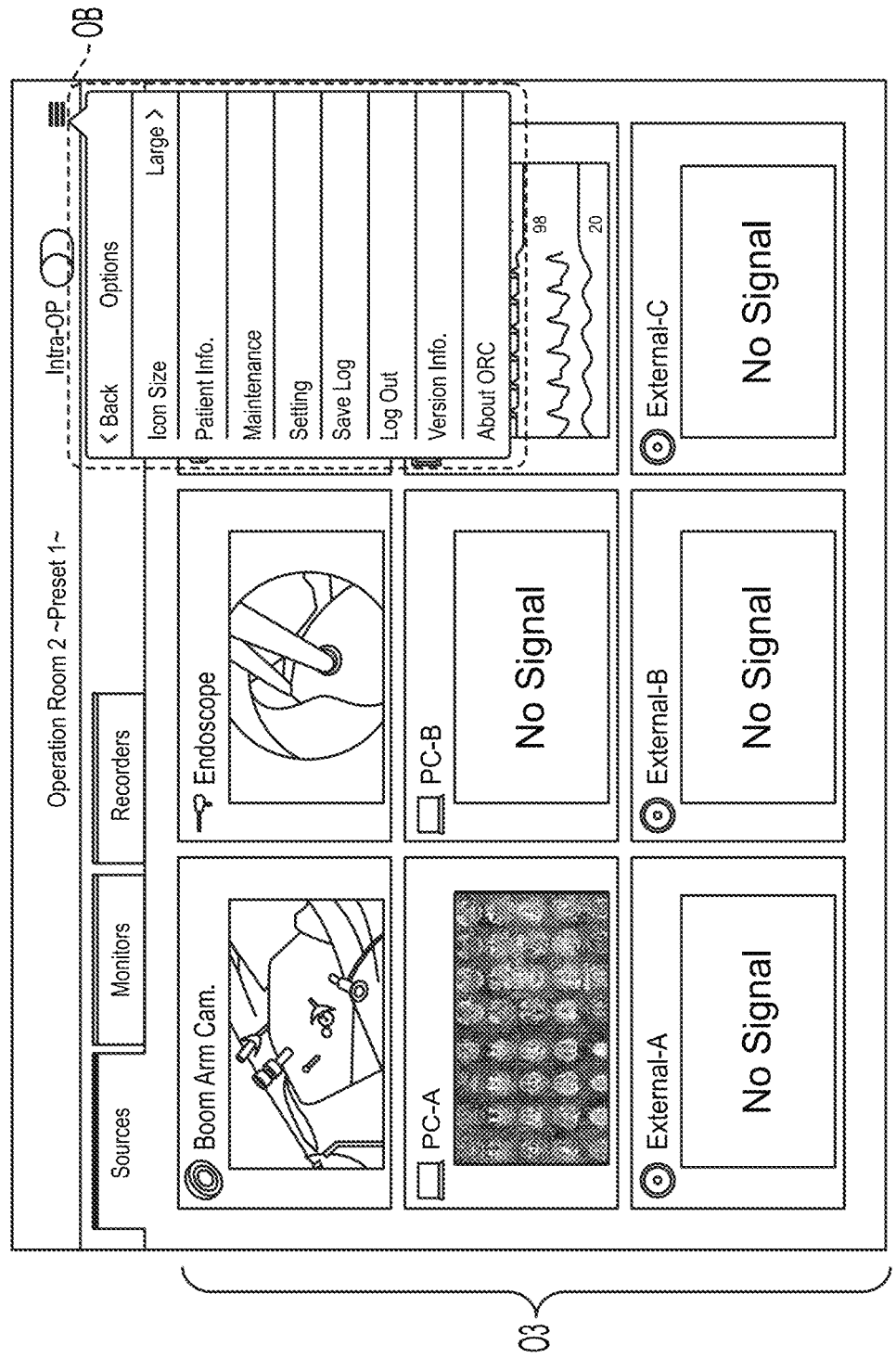
FIG. 8 is an explanatory diagram for explaining an example of display at the medical control system to which a control method according to the present embodiment is applied.

FIG. 8 illustrates an example of the context menu displayed in the case where the context menu button is manipulated. In the case where the context menu button is manipulated, as indicated in OB in FIG. 8, context menu associated with various kinds of manipulation and editing of data is displayed.

Further, in the case where the Intra-OP switch is put into an ON state which indicates that an operation is being performed, for example, manipulation with respect to the context menu is restricted. Examples of a method for restricting manipulation with respect to the context menu can include, for example, "making items to be restricted in the context menu grayed out so that manipulation cannot be performed", "disabling manipulation with respect to the context menu" (in this case, for example, the context menu itself is not displayed), or the like.

In the case where "Sources" is selected in the device category selection tab, the device selection screen, for example, as illustrated in FIG. 2 is displayed.

Figure 9:
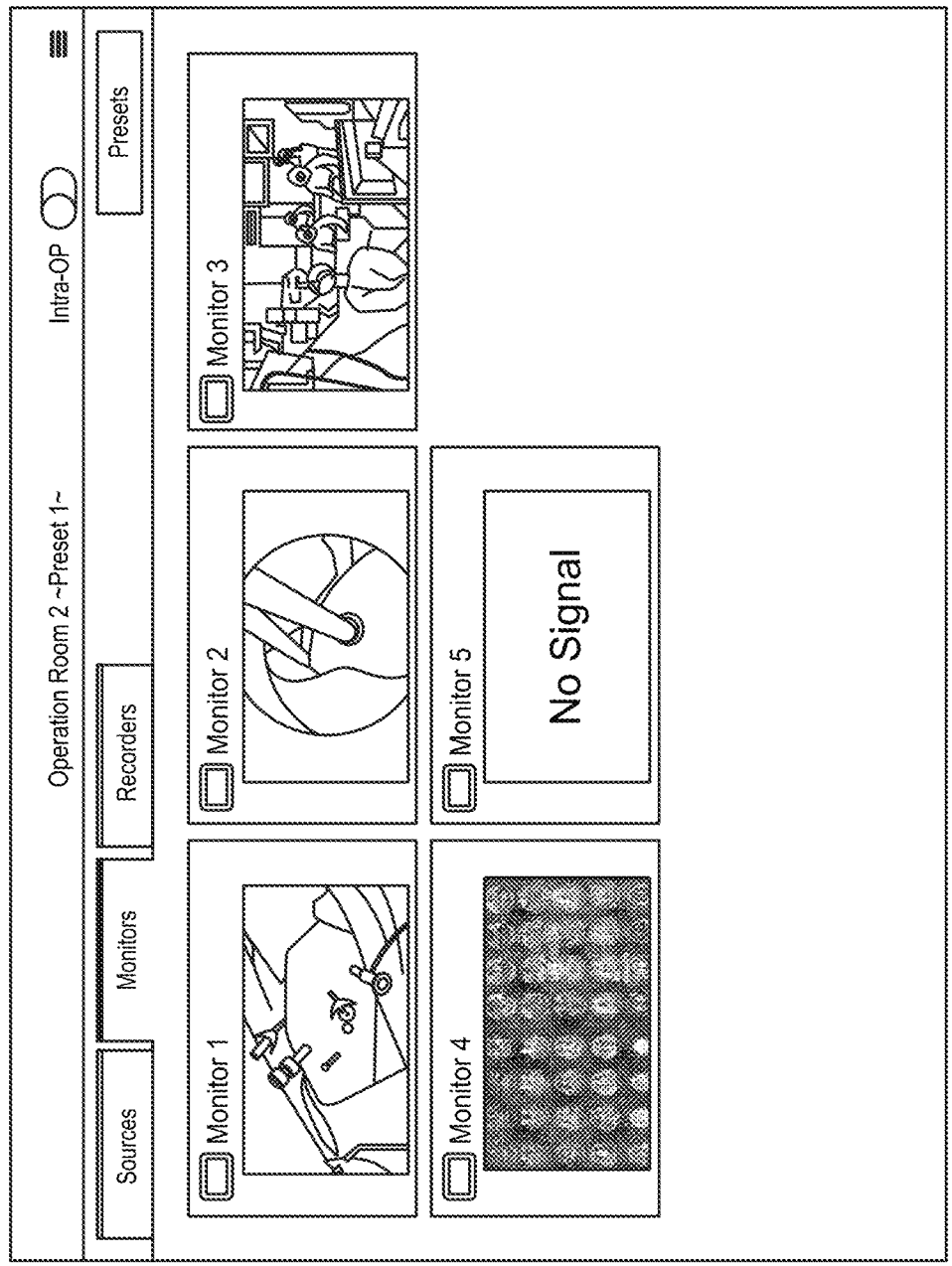
FIG. 9 is an explanatory diagram for explaining an example of display at the medical control system to which a control method according to the present embodiment is applied.

FIG. 9 illustrates another example of the device selection screen and illustrates a case where "Monitors" is selected in the device category selection tab.

Also in the case where "Monitors" is selected in the device category selection tab, the device selection screen has a configuration similar to that in the case where "Sources" is selected illustrated in FIG. 2.

Here, the device selection screen illustrated in FIG. 9 is different from the device selection screen illustrated in FIG. 2 in that "the screen transitions to a Monitors screen in the device control screen which will be described later by the device selection button being manipulated".

Further, while not illustrated, also in the case where "Recorders" is selected in the device category selection tab, the device selection screen has a configuration similar to that in the case where "Sources" is selected illustrated in FIG. 2.

Here, the device selection screen in the case where "Recorders" is selected in the device category selection tab is different from the device selection screen illustrated in FIG. 2 in that "the screen transitions to a Recorders screen in the device control screen which will be described later by the device selection button being manipulated".

(II) Device Control Screen

The device control screen will be described next. The device control screen corresponds to an example of a screen displayed through control processing associated with the control method according to the present embodiment. In the following description, control processing performed by the medical control apparatus 100 will be also described as appropriate.

Figure 10:
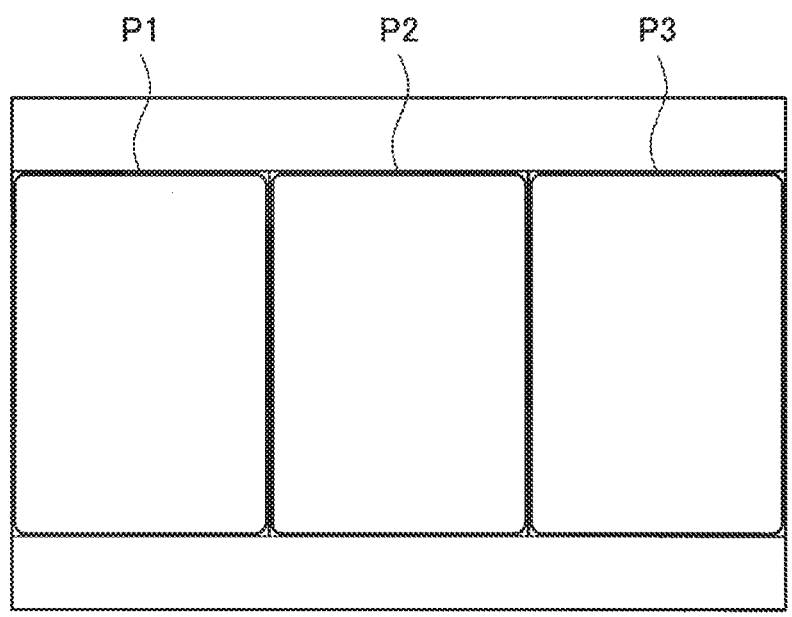
FIG. 10 is an explanatory diagram for explaining an example of display at the medical control system to which a control method according to the present embodiment is applied.

FIG. 10 is an explanatory diagram for explaining an example of display in the medical control system 1000 to which the control method according to the present embodiment is applied and illustrates an example of a configuration of the device control screen displayed on the display screen of the display target apparatus 500.

The device control screen is configured with, for example, the following three panes (display regions).

Device pane (hereinafter, indicated with reference numeral P1)

Control pane (hereinafter, indicated with reference numeral P2)

Connect pane (hereinafter, indicated with reference numeral P3)

Here, positions where the three panes are to be displayed change in accordance with, for example, types of the device control screen (for example, a Sources screen, a Monitors screen and a Recorders screen which will be described later).

Each of the Sources screen, the Monitors screen and the Recorders screen will be described below as an example of the device control screen.

(II-1) First Example of Device Control Screen: Sources Screen

FIG. 11 to FIG. 16 are explanatory diagrams for explaining an example of display in the medical control system 1000 to which the control method according to the present embodiment is applied. FIG. 11 to FIG. 16 each illustrates the whole of the device control screen or part of the device control screen displayed on the display screen of the display target apparatus 500.

The first example of the device control screen will be described below while referring to FIG. 11 to FIG. 16 as appropriate. Here, the first example of the device control screen corresponds to a "display example in the case where the first display region, the second display region and the third display region are displayed in one screen".

Figure 11:
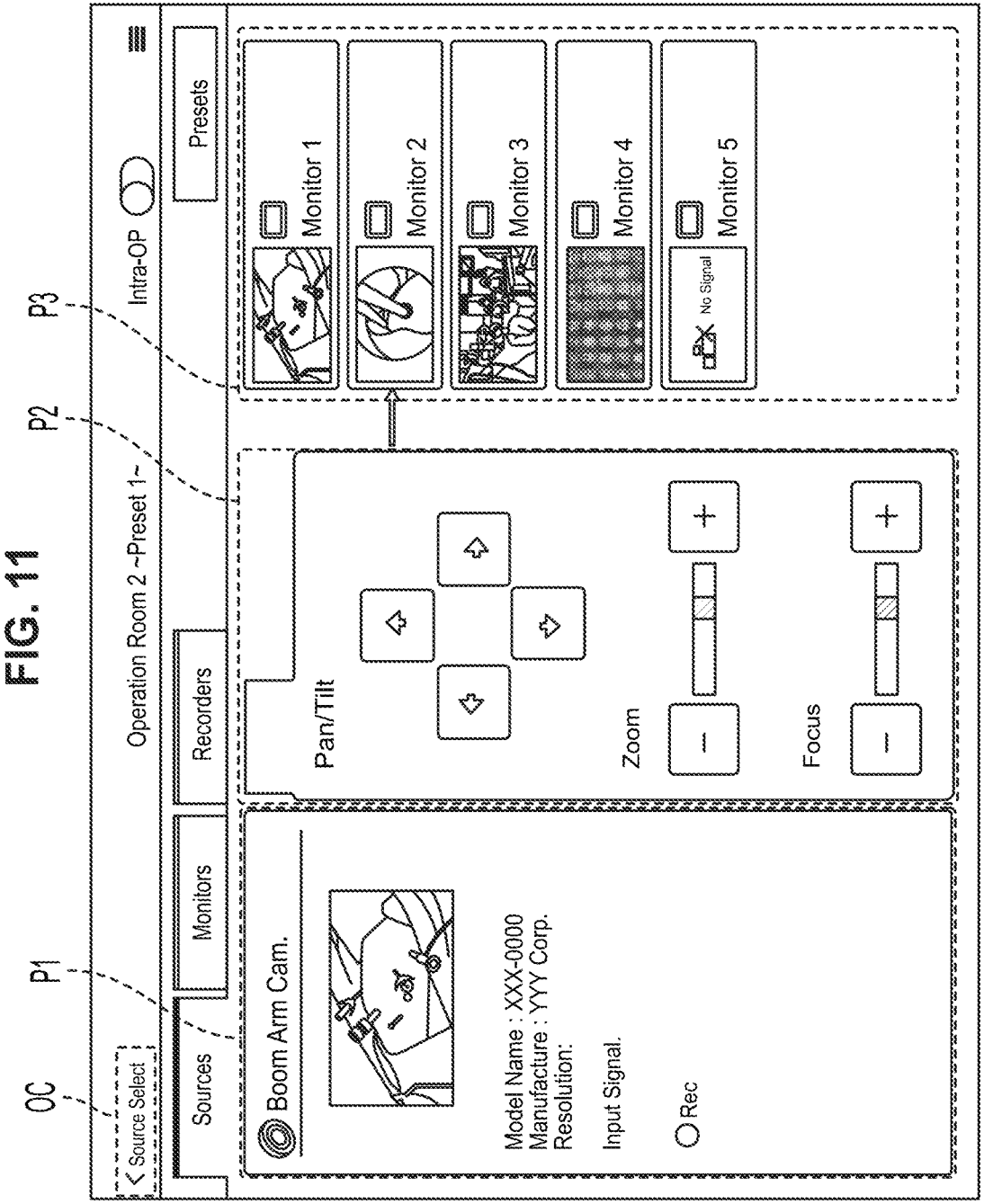
FIG. 11 is an explanatory diagram for explaining an example of display at the medical control system to which a control method according to the present embodiment is applied.

FIG. 11 illustrates an example of the Sources screen in the device control screen.

In the Sources screen illustrated in FIG. 11, for example, a button (OC illustrated in FIG. 11) for making the screen transition to the device selection screen in which "Sources" is selected in the device category selection tab is provided.

The user can select another device again in the device selection screen by manipulating the above-described button (OC illustrated in FIG. 11).

Further, the Sources screen illustrated in FIG. 11 includes the Device pane P1, the Control pane P2 and the Connect pane P3 from the left side in the display screen.

In the Device pane P1 illustrated in FIG. 11, information of the device corresponding to the device selection button (O3 illustrated in FIG. 2) selected in the device selection screen in which "Sources" is selected in the device category selection tab is displayed. Here, the Device pane P1 illustrated in FIG. 11 corresponds to an example of the first display region according to the present embodiment.

Figure 12:
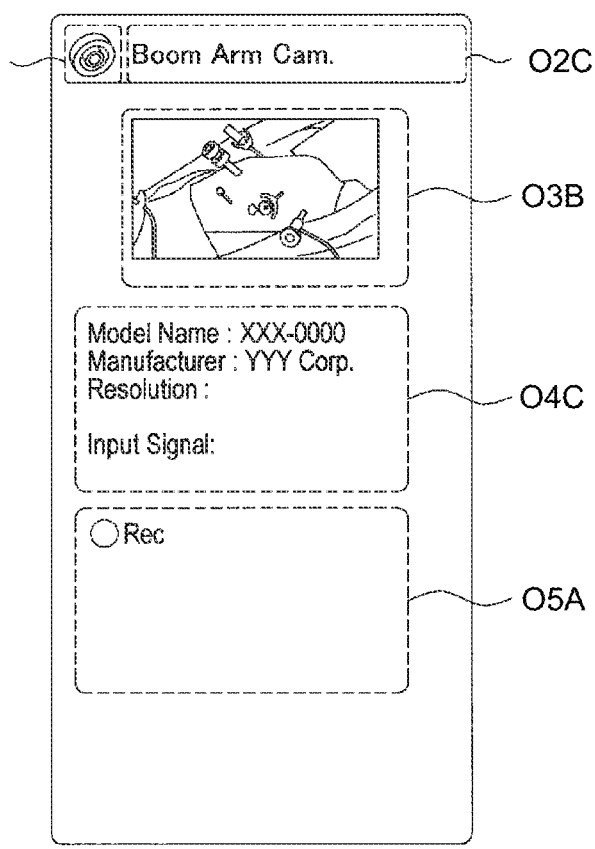
FIG. 12 is an explanatory diagram for explaining an example of display at the medical control system to which a control method according to the present embodiment is applied.

FIG. 12 illustrates an example of a configuration of the Device pane P1. The Device pane P1 includes, for example, an icon (O1B illustrated in FIG. 12), device name display (O2C illustrated in FIG. 12), a thumbnail image (O3B illustrated in FIG. 12), property display (O4C illustrated in FIG. 12) and status display (O5A illustrated in FIG. 12).

The icon (O1B illustrated in FIG. 12) is an icon indicating a type of the device.

The device name display (O2C illustrated in FIG. 12) indicates a name of the device. A region of the device name display (O2C illustrated in FIG. 12) is set so as to stretch over the width of the Device pane P1 so that, for example, long device name can be displayed.

The thumbnail image (O3B illustrated in FIG. 12) indicates an image output from a device which is an input source.

Here, while examples of the thumbnail image can include a still image, the thumbnail image may be a moving image. As described above, the thumbnail image according to the present embodiment can be regularly or irregularly updated. In the case where the thumbnail image is updated, it is possible to reflect an image most recently output from the input source in the thumbnail image.

Further, for example, in the case where a parameter of the device which is the input source is adjusted, or the like, in the Control pane P2 of the device control screen, an image output from the input source after the parameter is adjusted is reflected in the thumbnail image.

Further, in the case where a thumbnail image cannot be acquired, display as illustrated in FIG. 5B or FIG. 5C may be performed in the region for the thumbnail image.

The property display (O4C illustrated in FIG. 12) indicates, for example, information acquired from the device. FIG. 12 illustrates an example where model name and a manufacturer are displayed.

The status display (O5A illustrated in FIG. 12) indicates a state of the device, such as, for example, error display and an operation state.

Referring to FIG. 11 again, an example of the Sources screen in the device control screen will be described. In the Control pane P2 illustrated in FIG. 11, objects for controlling the device indicated in the Device pane P1 are displayed. Here, the Control pane P2 illustrated in FIG. 11 corresponds to an example of the third display region according to the present embodiment. Further, because the Device pane P1 corresponds to an example of the first display example according to the present embodiment, it can be said that the Control pane P2 illustrated in FIG. 11 is a display region where objects for controlling the input source apparatus 200 are to be displayed.

Figure 13:
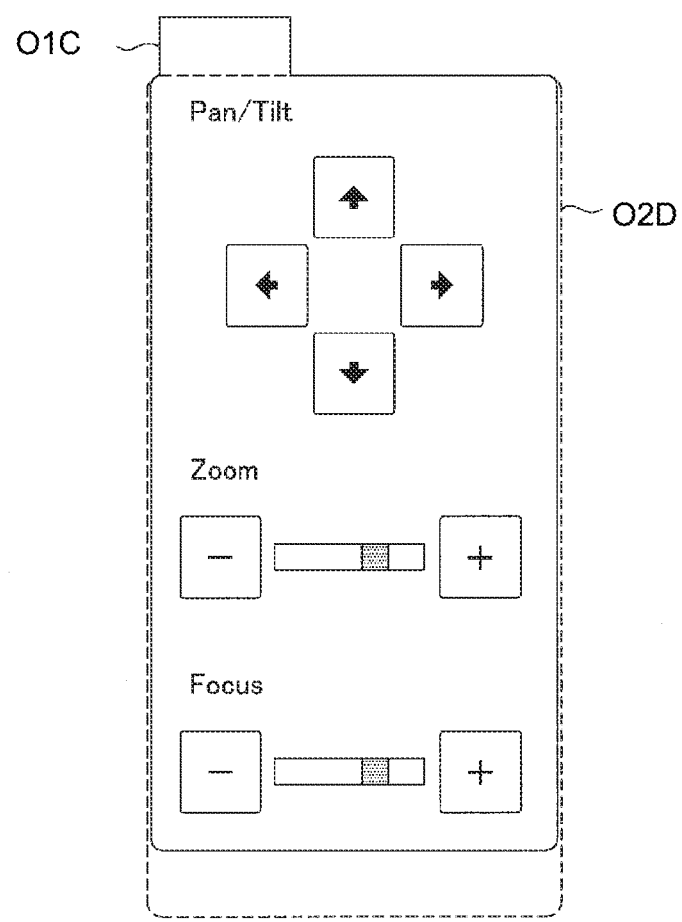
FIG. 13 is an explanatory diagram for explaining an example of display at the medical control system to which a control method according to the present embodiment is applied.

FIG. 13 illustrates an example of a configuration of the Control pane P2. The Control pane P2 includes, for example, a Control tab (O1C illustrated in FIG. 13) and a parameter editing region (O2D illustrated in FIG. 13).

The Control tab (O1C illustrated in FIG. 13) is a tab for each category of control. While FIG. 11 illustrates an example where one Control tab is provided in the Control pane P2, a plurality of Control tabs may be provided.

In the parameter editing region (O2 illustrated in FIG. 13), an object for manipulating the device indicated in the Device pane P1 and an object for adjusting a parameter of the device indicated in the Device pane P1 are displayed. In the parameter editing region (O2 illustrated in FIG. 13) illustrated in FIG. 13, an example is illustrated where a button for performing pan operation and tilt operation, an adjustment button and an adjustment slide bar for adjusting a zoom amount and an adjustment button and an adjustment slide bar for adjusting a focus amount are provided.

Note that, in the case where the whole objects cannot be displayed within the parameter editing region (O2 illustrated in FIG. 13), it may be possible to scroll display the objects. Further, a current zoom amount, a current focus amount, or the like, may be displayed with numerical values in the parameter editing region (O2 illustrated in FIG. 13). Further, items to be displayed in the parameter editing region (O2 illustrated in FIG. 13) can differ in accordance with a type of the device indicated in the Device pane P1.

Referring to FIG. 11 again, an example of the Sources screen in the device control screen will be described. In the Connect pane P3 illustrated in FIG. 11, objects relating to the output destination apparatus 300, at which an image output from the device indicated in the Device pane P1 can be displayed are displayed. Here, the Connect pane P3 illustrated in FIG. 11 corresponds to an example of the second display region according to the present embodiment. Further, because the Device pane P1 corresponds to an example of the first display region according to the present embodiment, it can be said that the Connect pane P3 illustrated in FIG. 11 is a display region where objects relating to the output destination apparatus 300 at which an image of the input source apparatus 200 can be displayed are to be displayed.

FIG. 14 illustrates an example of a configuration of the Connect pane P3. The Connect pane P3 includes, for example, display of a list of connection destinations (O1D illustrated in FIG. 14) and connection display (O2E illustrated in FIG. 14).

The display of a list of connection destinations (O1D illustrated in FIG. 14) indicates a list of output destination apparatuses 300 at which an image output from the device indicated in the Device pane P1 can be displayed. Examples of the output destination apparatuses 300 displayed in the display of a list of connection destinations (O1D illustrated in FIG. 14) can include, for example, the output destination apparatus 300 for which normal connection with the device indicated in the Device pane P1 is ensured upon construction (or updating) of the medical control system 1000.

Further, the display of a list of connection destinations (O1D illustrated in FIG. 14) includes, for example, a "thumbnail image corresponding to the image displayed at the output destination apparatus 300", an "icon indicating the output destination apparatus 300" and "device name display of the output destination apparatus 300".

Here, while examples of the thumbnail image can include a still image, the thumbnail image may be a moving image. As described above, the thumbnail image according to the present embodiment can be regularly or irregularly updated. In the case where the thumbnail image is updated, it is possible to reflect an image most recently input to the output destination apparatus 300 in the thumbnail image. Further, for example, in the case where a parameter of the input source apparatus 200 is adjusted, or the like, in the Control pane P2 of the device control screen illustrated in FIG. 13, in the thumbnail image corresponding to the output destination apparatus 300 at which an image output from the input source apparatus 200 is displayed, an image output from the input source apparatus 200 after the parameter is adjusted is reflected.

Further, in the case where the thumbnail image cannot be acquired, display as illustrated in FIG. 5B or FIG. 5C may be performed in the region for the thumbnail image.

The medical control apparatus 100 can display a thumbnail image of the image displayed on the display screen of the output destination in the Connect pane P3 corresponding to the second display region, for example, as the display of a list of connection destinations (O1D illustrated in FIG. 14) illustrated in FIG. 14.

The connection display (O2 illustrated in FIG. 14) indicates the output destination apparatus 300 selected through user manipulation with respect to the Connect pane P3.

FIG. 14 illustrates an example where the selected output destination apparatus 300 is indicated with an arrow. Note that a method for specifying the selected output destination apparatus 300 is not limited to the example illustrated in FIG. 14. Further, in the case where a plurality of output destination apparatuses 300 are selected through user manipulation with respect to the Connect pane P3, a plurality of types of connection display are displayed in the Connect pane P3.

Here, example of the user manipulation with respect to the Connect pane P3 can include, for example, the following examples. Note that, it goes without saying that the examples of the user manipulation with respect to the Connect pane P3 are not limited to the following examples.

Manipulation of touching the Connect pane P3 (in the case where a display device of the display target apparatus 500 is a touch panel)

Manipulation using a manipulation device such as a physical button, provided at the display target apparatus 500 or an external manipulation device such as a remote controller.

The medical control apparatus 100 causes the output destination apparatus 300 at which the image of the input source apparatus 200 is to be displayed, selected through manipulation with respect to the second display region on the basis of manipulation with respect to the Connect pane P3 corresponding to the second display region, to be specified, for example, as the connection display (O2 illustrated in FIG. 14) illustrated in FIG. 14.

Note that the Sources screen in the device control screen is not limited to the example illustrated in FIG. 11.

FIGS. 15A, 15B, and 15C illustrate an example of an image to be output from the device indicated in the Device pane P1.

There can be a case where an image to be output from the device indicated in the Device pane P1 includes, for example, an image with higher resolution than that of an image with 2K resolution or an image with high definition (HD) resolution, such as an image with 4K resolution and an image with 8K resolution.

Here, in the case where the image to be output from the device indicated in the Device pane P1 is an image with high resolution as described above, it is assumed that "a user such as a healthcare professional desires to display an image corresponding to part of the image illustrated in FIG. 15A, for example, as illustrated in FIG. 15B and FIG. 15C at a different output destination apparatus 300".

Therefore, the Sources screen in the device control screen may be a screen which enables an image corresponding to part of the image to be displayed at a different output destination apparatus 300 on the basis of the user manipulation. By causing an image corresponding to part of the image to be displayed at a different output destination apparatus 300, for example, it is possible to "cause an image obtained by changing an angle of view of the image of one input source apparatus 200 to be displayed at a different output destination apparatus 300".

Figure 16:
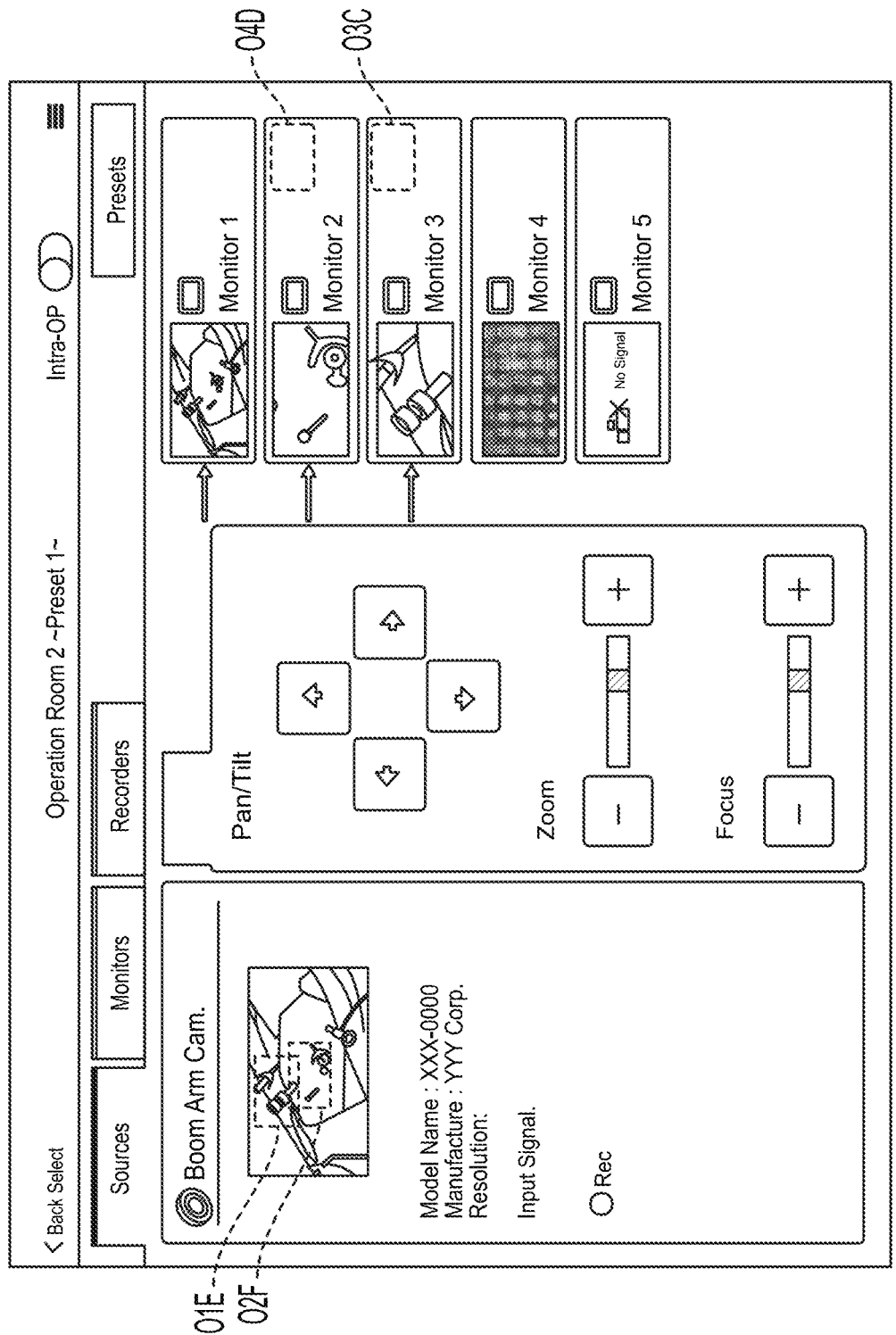
FIG. 16 is an explanatory diagram for explaining an example of display at the medical control system to which a control method according to the present embodiment is applied.

FIG. 16 illustrates another example of the Sources screen in the device control screen.

While the configuration of the Sources screen illustrated in FIG. 16 is basically similar to the configuration of the Sources screen illustrated in FIG. 11, there is a difference in that "the output destination apparatus 300 at which an image corresponding to part of the image output from the device indicated in the Device pane P1 is to be displayed is specified".

For example, in the case where part of the thumbnail image is selected as illustrated in O1E and O2F in FIG. 16 through user manipulation with respect to the Device pane P1 and the output destination apparatus 300 is selected through user manipulation with respect to the Connect pane P3, as illustrated in O3C and O4D in FIG. 16, the output destination apparatus 300 at which an image of the selected part of the thumbnail image is to be displayed is further specified.

Here, examples of the user manipulation with respect to the Device pane PI can include, for example, the following examples. Note that, it goes without saying that the examples of the user manipulation with respect to the Device pane P1 are not limited to the following examples.

Manipulation which can select a region on a display screen, such as pinch manipulation with respect to a thumbnail image of the Device pane P1 (in the case where the display device of the display target apparatus 500 is a touch panel)

Manipulation using a manipulation device such as a physical button, provided at the display target apparatus 500 or an external manipulation device such as a remote controller The medical control apparatus 100 may further cause the "output destination apparatus 300 at which an image corresponding to part of the image of the input source apparatus 200 selected through manipulation with respect to the Device pane P1 is to be displayed, and which is selected through manipulation with respect to the Connect pane P3, to be specified" on the basis of manipulation with respect to the Device pane P1 corresponding to the first display region and manipulation with respect to the Connect pane P3 corresponding to the second display region, for example, as 01E to 04D illustrated in FIG. 16.

(II-2) Second Example of Device Control Screen: Monitors Screen

FIGS. 17, 18A, 18B, 18C, and 18D are explanatory diagrams for explaining an example of display in the medical control system 1000 to which the control method according to the present embodiment is applied. FIGS. 17, 18A, 18B, 18C, and 18D each illustrate the whole of the device control screen or part of the device control screen displayed on the display screen of the display target apparatus 500.

A second example of the device control screen will be described below while referring to FIGS. 17, 18A, 18B, 18C, and 18D as appropriate. Here, the second example of the device control screen corresponds to a "display example in the case where the first display region and the third display region are displayed in one screen".

Figure 17:
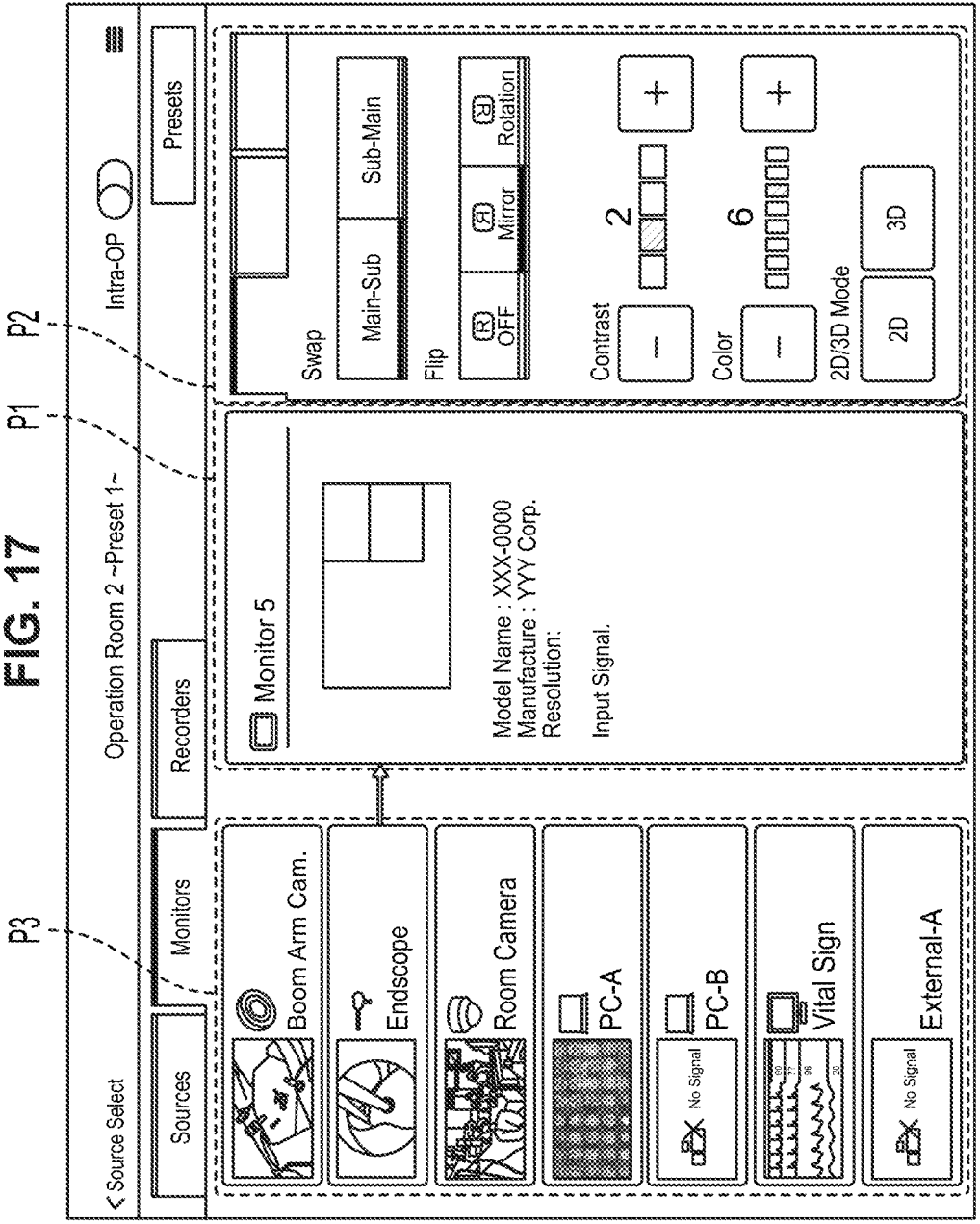
FIG. 17 is an explanatory diagram for explaining an example of display at the medical control system to which a control method according to the present embodiment is applied.
Figure 18A:
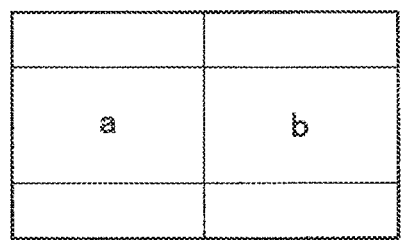
FIGS. 18A, 18B, 18C, and 18D are explanatory diagrams for explaining an example of display at the medical control system to which a control method according to the present embodiment is applied.
Figure 18B:
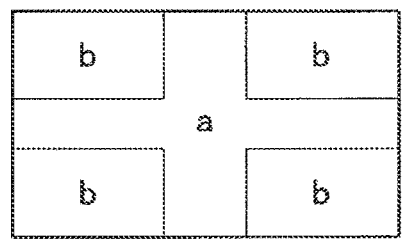
Figure 18C:
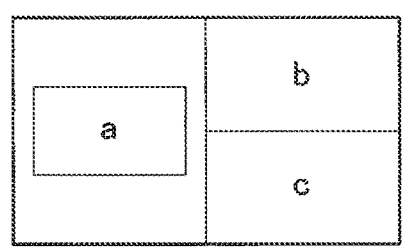
Figure 18D:
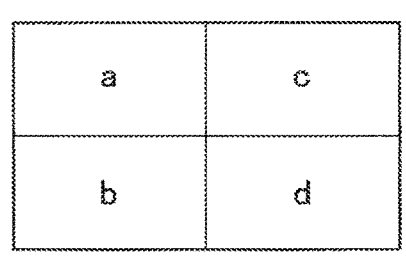

FIG. 17 illustrates an example of the Monitors screen in the device control screen.

The Monitors screen illustrated in FIG. 17 includes the Connect pane P3, the Device pane P1 and the Control pane P2 from the left side of the display screen.

In the Connect pane P3 illustrated in FIG. 17, objects relating to the input source apparatus 200, which can be displayed at the output destination apparatus 300 selected in the device selection screen in which "Monitors" is selected in the device category selection tab, are displayed. Here, the Connect pane P3 illustrated in FIG. 17 corresponds to an example of the first display region according to the present embodiment.

FIG. 17 illustrates an example where a list of objects respectively relating to the input source apparatuses 200 is displayed in the Connect pane P3. Examples of the objects relating to the input source apparatuses 200 can include, for example, a thumbnail image, an icon and device name display as with the case of the display of a list of connection destinations (O1D illustrated in FIG. 14) illustrated in FIG. 14.

Further, examples of the input source apparatus 200 displayed in the Connect pane P3 can include, for example, the input source apparatus 200 for which normal connection with the device indicated in the Device pane P1 is ensured upon construction (or updating) of the medical control system 1000.

In the Device pane P1 illustrated in FIG. 17, information of the device corresponding to the device selection button selected in the device selection screen in which "Monitors" is selected in the device category selection tab is displayed. Here, the configuration of the Device pane P1 illustrated in FIG. 17 is similar to the configuration of the Device pane P1, for example, illustrated in FIG. 12.

In the Control pane P2 illustrated in FIG. 17, objects for controlling the device indicated m the Device pane P1 are displayed. Here, the Control pane P2 illustrated in FIG. 17 corresponds to an example of the third display region according to the present embodiment. Further, the device indicated in the Device pane P1 is the output destination apparatus 300 selected in the device selection screen in which "Monitors" is selected in the device category selection tab. Therefore, it can be said that the Control pane P2 illustrated in FIG. 17 is a display region where objects for controlling the output destination apparatus 300 are to be displayed.

Examples of the objects for controlling the device indicated in the Device pane P1, displayed in the Control pane P2 of the Monitors screen in the device control screen can include the following examples.

Button indicated as "Swap" in FIG. 17: a button for switching between a main display region and a sub display region in the case where the device indicated in the Device pane P1 has a PinP function (function of allowing a plurality of display regions in which images can be independently displayed to be provided in one screen)

Button indicated as "Flip" in FIG. 17: a button for controlling a direction of display in the device indicated in the Device pane P1

Adjustment button indicated as "Contrast" in FIG. 17: a button for adjusting contrast in the device indicated in the Device pane P1

Adjustment button indicated as "Color" in FIG. 17: a button for adjusting luminance, color phase or balance of RGB in the device indicated in the Device pane P1

Button indicated as "2D/3D Mode" in FIG. 17: a button for controlling switching of a display mode associated with stereoscopic view in the device indicated in the Device pane P1

Note that the objects for controlling the device indicated in the Device pane P1, displayed in the Control pane P2 of the Monitors screen in the device control screen are not limited to the above-described examples.

For example, in the case where the device indicated in the Device pane P1 has a PinP function, in the Control pane P2 of the Monitors screen in the device control screen, an object for changing a configuration of the display region in the PinP function may be further displayed. Note that the object for changing the configuration of the display region in the PinP function can be also displayed in other panes such as the Device pane P1. In the case where the object for changing the configuration of the display region in the PinP function is displayed in a pane other than the Control pane P2 illustrated in FIG. 17, the pane in which the object for changing the configuration of the display region in the PinP function is displayed plays a role as the third display region according to the present embodiment.

Examples of the configuration of the display region in the PinP function can include, for example, examples illustrated in FIGS. 18A, 18B, 18C, and 18D. In FIGS. 18A, 18B, 18C, and 18D, the display regions indicated with "a", "b", "c" and "d" correspond to the display regions in the PinP function In the case where the device indicated in the Device pane P1 corresponding to the output destination apparatus 300 has a PinP function, the medical control apparatus 100 may cause an "object for controlling display in one or more of display regions associated with PinP in the output destination apparatus 300 to be displayed in the Control pane P2 corresponding to the third display region", for example, as the button indicated as "Swap" in FIG. 17.

Further, an object for controlling the device indicated in the Device pane P1, displayed m the Control pane P2 of the Monitors screen in the device control screen can differ in accordance with a type of the device indicated in the Device pane P1.

For example, in the case where the device indicated in the Device pane P1 does not have a PinP function, the button indicated as "Flip" in FIG. 17 does not have to be displayed.

(II-3) Third Example of Device Control Screen: Recorders Screen

Figure 19A:
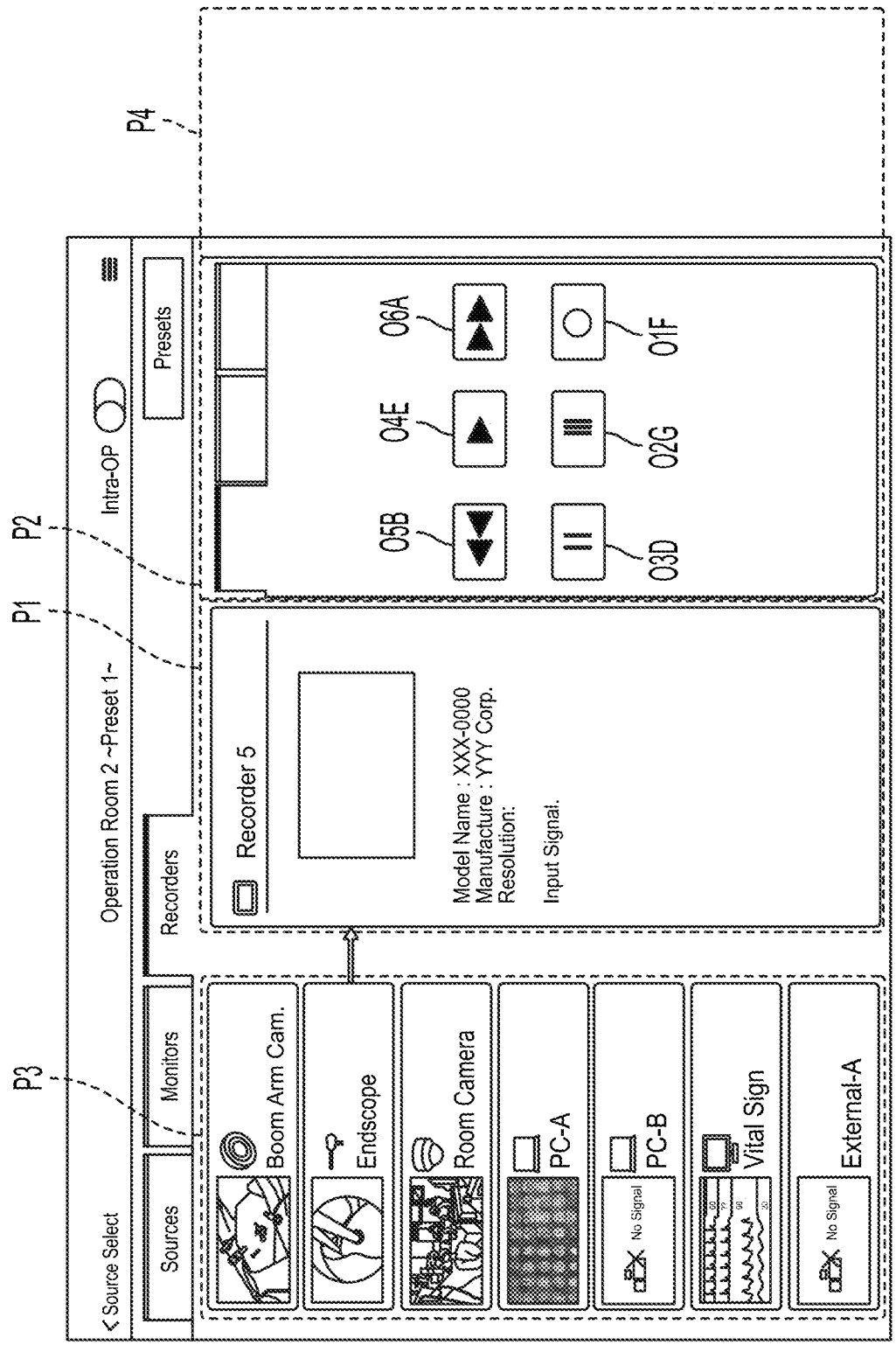
FIG. 19A is an explanatory diagram for explaining an example of display at the medical control system to which a control method according to the present embodiment is applied.

FIG. 19A and FIG. 19B are explanatory diagrams for explaining an example of display m the medical control system 1000 to which the control method according to the present embodiment is applied. FIG. 19A and FIG. 19B each illustrates the whole of the device control screen displayed on the display screen of the display target apparatus 500. The screen is switched between the device control screen illustrated in FIG. 19A and the device control screen illustrated in FIG. 19B through user manipulation.

A third example of the device control screen will be described below while referring to FIG. 19A and FIG. 19B as appropriate. Here, the third example of the device control screen illustrated in FIG. 19A corresponds to the "display example in the case where the first display region and the third display region are displayed in one screen". Further, the third example of the display control screen illustrated in FIG. 19B corresponds to the "display example in the case where the second display region and the third display region are displayed in one screen".

FIG. 19A illustrates an example of the Recorders screen in the device control screen.

The Recorders screen illustrated in FIG. 19A includes the Connect pane P3, the Device pane P1 and the Control pane P2 from the left side of the display screen in a similar manner to the Monitors screen illustrated in FIG. 17.

In the Connect pane P3 illustrated in FIG. 19A, objects relating to the input source apparatus 200 which can output an image signal to the apparatus 400 selected in the device selection screen in which "Recorders" is selected in the device category selection tab are displayed. Here, the Connect pane P3 illustrated in FIG. 19A corresponds to an example of the first display region according to the present embodiment.

FIG. 19A illustrates an example where a list of objects each relating to the input source apparatus 200 is displayed in the Connect pane P3 as with the case of FIG. 17. Further, examples of the input source apparatus 200 displayed in the Connect pane P3 illustrated in FIG. 19A can include, for example, the input source apparatus 200 for which normal connection with the device indicated in the Device pane P1 is ensured upon construction (or updating) of the medical control system 1000.

In the Device pane P1 illustrated in FIG. 19A, information of the device corresponding to the device selection button selected in the device selection screen in which "Recorders" is selected in the device category selection tab is displayed. Here, the configuration of the Device pane P1 illustrated in FIG. 19A is similar to the configuration of the Device pane P1, for example, illustrated in FIG. 12.

In the Control pane P2 illustrated in FIG. 19A, objects for controlling the device indicated in the Device pane P1 are displayed. Here, the Control pane P2 illustrated in FIG. 19A corresponds to an example of the third display region according to the present embodiment. Further, the device indicated in the Device pane P1 is the apparatus 400 selected in the device selection screen in which "Recorders" is selected in the device category selection tab. Therefore, it can be said that the Control pane P2 illustrated in FIG. 19A is a display region where the objects for controlling the apparatus 400 are to be displayed.

Examples of the objects for controlling the device indicated in the Device pane P1, which are displayed in the Control pane P2 of the Recorders screen in the device control screen can include the following examples. Note that, it goes without saying that the examples of the objects for controlling the device indicated in the Device pane P1, which are displayed in the Control pane P2 of the Recorders screen in the device control screen are not limited to the following examples.

Recording button for starting recording of image data in a recording medium (O1F illustrated in FIG. 19A)
Stop button for stopping processing being performed (O2G illustrated in FIG. 19A)
Pause button for pausing processing being performed (O3D illustrated in FIG. 19A)
Reproduction button for starting reproduction of image data stored in a recording medium (O4E illustrated in FIG. 19A)
Rewind button for rewinding an image being reproduced (O5B illustrated in FIG. 19A)
Fast-forward button for fast-forwarding an image being reproduced (O6A illustrated in FIG. 19A)

According to the device control screen illustrated in FIG. 19A, it is, for example, possible to control recording of image data in the device indicated in the Device pane P1 from the input source apparatus 200 selected through user manipulation with respect to the Connect pane P3.

FIG. 19B illustrates another example of the Recorders screen in the device control screen.

The Recorders screen illustrated in FIG. 19B includes the Device pane P1, the Control pane P2 and the Connect pane P4 from the left side of the display screen.

The Device pane P1 illustrated in FIG. 19B and the Control pane P2 illustrated in FIG. 19B are respectively the same as the Device pane P1 illustrated in FIG. 19A and the Control pane P2 illustrated in FIG. 19A. Here, the Control pane P2 illustrated in FIG. 19B corresponds to an example of the third display region according to the present embodiment. Further, the device indicated in the Device pane P1 is the apparatus 400 selected in the device selection screen in which "Recorders" is selected in the device category selection tab. Therefore, it can be said that the Control pane P2 illustrated in FIG. 19B is a display region where the objects for controlling the apparatus 400 are to be displayed.

In the Connect pane P4 illustrated in FIG. 19B, objects relating to the output destination apparatus 300 at which an image output from the device indicated in the Device pane P1 can be displayed are displayed as with the case of the Connect pane P3 illustrated in FIG. 11 and FIG. 14. Here, the Connect pane P4 illustrated in FIG. 19B corresponds to an example of the second display region according to the present embodiment.

As described above, the Connect pane P4 illustrated in FIG. 19B corresponds to the second display region according to the present embodiment as with the case of the Connect pane P3 illustrated in FIG. 11 and FIG. 14. Therefore, the medical control apparatus 100 can cause a thumbnail image of the image displayed on the display screen of the output destination to be displayed in the Connect pane P4 corresponding to the second display region as with the case of the Connected pane P3 illustrated in FIG. 11 and FIG. 14.

According to the device control screen illustrated in FIG. 19B, it is, for example, possible to cause the image reproduced in the device indicated in the Device pane P1 to be displayed at the output destination apparatus 300 selected through user manipulation with respect to the Connect pane P4.

Here, among the apparatuses 400 selected in the device selection screen in which "Recorders" is selected in the device category selection tab, there can exist an apparatus having both an image recording function and an image reproducing function, that is, an apparatus which functions as the output destination and the input source.

In order to control the apparatus 400 which functions as the output destination and the input source as described above, one of the device control screen illustrated in FIG. 19A and the device control screen illustrated in FIG. 19B is insufficient.

Here, for example, if the Connect pane P4 illustrated in FIG. 19B is further displayed on the device control screen illustrated in FIG. 19A, it is possible to sufficiently control the apparatus 400 which functions as the output destination and the input source as described above. However, in the case where a size or resolution of the display screen is not large enough, such as in the case where the display target apparatus 500 is a tablet type apparatus, there is a possibility that visibility degrades by the Connect pane P4 illustrated in FIG. 19B being further displayed in the device control screen illustrated in FIG. 19A.

Therefore, the medical control apparatus 100 causes the screen to be switched between, for example, the device control screen illustrated in FIG. 19A and the device control screen illustrated in FIG. 19B and displayed on the basis of user manipulation.

Here, examples of the user manipulation for switching display of the device control screen can include, for example, the following examples. Note that, it goes without saying that the examples of the user manipulation for switching the display of the device control screen are not limited to the following examples.

Manipulation which can switch the display of the display screen, such as manipulation of swiping the display screen (in the case where the display device of the display target apparatus 500 is a touch panel)

Manipulation using a manipulation device such as a physical button provided at the display target apparatus 500 or an external manipulation device such as a remote controller By the medical control apparatus 100 causing the screen to be switched between the device control screen illustrated in FIG. 19A and the device control screen illustrated in FIG. 19B and displayed, it becomes possible to prevent degradation of visibility and sufficiently control the apparatus 400 which functions as the output destination and the input source as described above.

[3] Example of Effects Provided by Control Method According to Present Embodiment being Used By the medical control apparatus 100 performing the control processing associated with the control method according to the present embodiment, for example, the following effects are provided. Note that, it goes without saying that the effects provided by the control method according to the present embodiment being used are not limited to the following effects.

For example, by the device control screens illustrated in FIG. 11, FIG. 17, FIG. 19A and FIG. 19B being used, because switching of an image and control of equipment can be performed in one screen, the user can efficiently work.

For example, as illustrated in the Connect pane P3 in FIG. 11, the Connect pane P3 in FIG. 17, the Connect pane P3 in FIG. 19A and the Connect pane P4 in FIG. 19B, because only equipment for which an image can be switched is displayed in the device control screen, it is possible to prevent erroneous manipulation by the user.

Also at equipment at which a signal source and an output destination change in accordance with processing to be performed (processing corresponding to purpose of use of a recorder) as the recorder (an example of the apparatus 400), for example, as described with reference to FIG. 19A and FIG. 19B, the user can perform common manipulation by switching a mode through user manipulation such as swipe manipulation.

For example, as described with reference to FIGS. 15A, 15B, 15C and FIG. 16, a plurality of images obtained by changing an angle of view of one image can be output to respectively different monitors (an example of the output destination).

(Medical Control Apparatus According to Present Embodiment)

An example of a configuration of the medical control apparatus according to the present embodiment which can perform the above-described processing associated with the control method according to the present embodiment will be described next.

Figure 20:
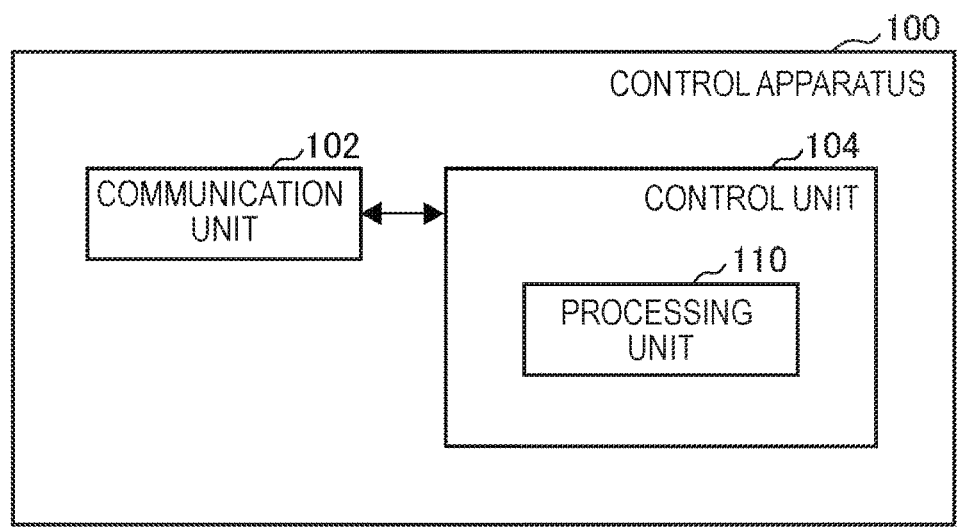
FIG. 20 is a block diagram illustrating an example of a configuration of a medical control apparatus according to the present embodiment.

FIG. 20 is a block diagram illustrating an example of the configuration of the medical control apparatus 100 according to the present embodiment. The medical control apparatus 100 includes, for example, a communication unit 102 and a control unit 104.

Further, the medical control apparatus 100 may include, for example, a read only memory (ROM, not illustrated), a random access memory (RAM, not illustrated), a storage unit (not illustrated), an operation unit (not illustrated) which can be manipulated by the user, a display unit (not illustrated) which displays various screens on the display screen, or the like. The medical control apparatus 100, for example, connects the above-described components with a bus which is a data transmission path.

The ROM (not illustrated) stores control data such as a program and an operation parameter to be used by the control unit 104. The RAM (not illustrated) temporarily stores a program to be executed by the control unit 104.

The storage unit (not illustrated) stores, for example, various kinds of data such as data associated with the control method according to the present embodiment and application. Here, examples of the storage unit (not illustrated) can include, for example, a recording medium such as a non-volatile memory. Further, the storage unit (not illustrated) may be, for example, detachable from the medical control apparatus 100.

Examples of the operation unit (not illustrated) can include, for example, an operation input device which will be described later. Further, examples of the display unit (not illustrated) can include a display device which will be described later.

[Hardware Configuration Example of Medical Control Apparatus 100]

Figure 21:
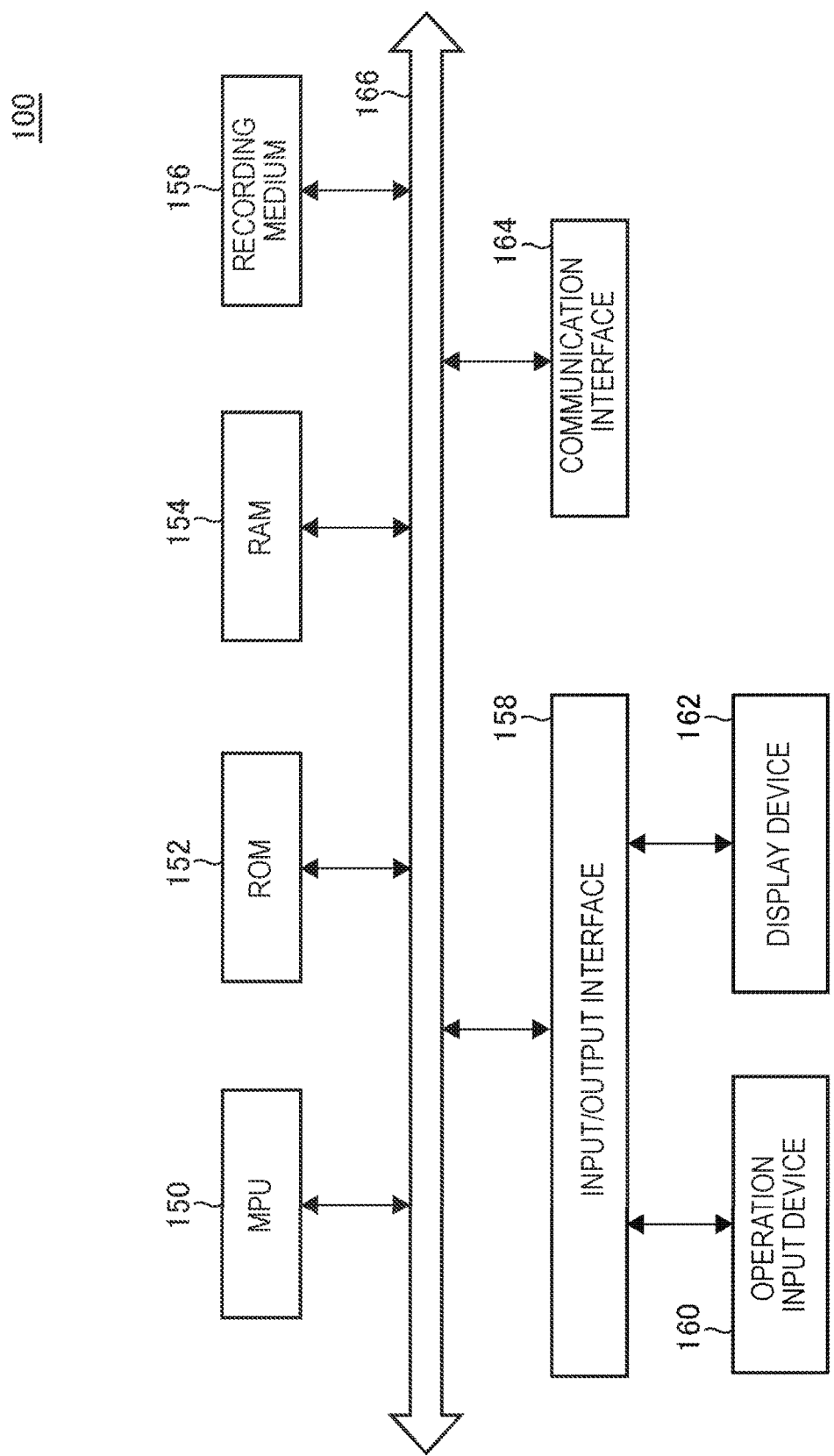
FIG. 21 is an explanatory diagram illustrating an example of a hardware configuration of the medical control apparatus according to the present embodiment.

FIG. 21 is an explanatory diagram illustrating an example of a hardware configuration of the medical control apparatus 100 according to the present embodiment. The medical control apparatus 100 includes, for example, an MPU 150, a ROM 152, a RAM 154, a recording medium 156, an input/output interface 158, an operation input device 160, a display device 162 and a communication interface 164. Further, the medical control apparatus 100, for example, connects respective components with a bus 166 which is a data transmission path.

The MPU 150 is configured with, for example, one or more processors configured with an arithmetic circuit such as an MPU, various kinds of processing circuits, or the like, and functions as a control unit (not illustrated) which controls the whole medical control apparatus 100. Further, the MPU 150 plays a role of, for example, a processing unit 110 in the medical control apparatus 100. Note that the processing unit 110 may be configured with a dedicated (or general-purpose) circuit (such as, for example, a processor separate from the MPU 150) which can implement processing at the processing unit 110.

The ROM 152 stores control data such as a program and an operation parameter to be used by the MPU 150. The RAM 154 temporarily stores a program, or the like, to be executed by the MPU 150.

The recording medium 156, which functions as a storage unit (not illustrated), for example, stores data associated with the control method according to the present embodiment and various kinds of data such as various kinds of application. Here, examples of the recording medium 156 can include, for example, a magnetic recording medium such as a hard disk, and a non-volatile memory such as a flash memory. Further, the recording medium 156 may be detachable from the medical control apparatus 100.

The input/output interface 158, for example, connects the operation input device 160 and the display device 162. The operation input device 160 functions as an operation unit (not illustrated), and the display device 162 functions as a display unit (not illustrated). Here, examples of the input/output interface 158 can include, for example, a universal serial bus (USB) terminal, a digital visual interface (DVI) terminal, a high-definition multimedia interface (HDMI) (registered trademark) terminal, various kinds of processing circuits, or the like.

Further, the operation input device 160 is, for example, provided on the medical control apparatus 100 and is connected to the input/output interface 158 inside the medical control apparatus 100. Examples of the operation input device 160 can include, for example, a button, a direction key, a rotary selector such as a jog dial, combination thereof, or the like.

Further, the display device 162 is, for example, provided on the medical control apparatus 100 and is connected to the input/output interface 158 inside the medical control apparatus 100. Examples of the display device 162 can include, for example, a liquid crystal display, an organic electroluminescence (EL) display, an organic light emitting diode (OLED) display, or the like.

Note that, it goes without saying that the input/output interface 158 can be connected to an external device such as an external operation input device (such as, for example, a keyboard and a mouse) and an external display device of the medical control apparatus 100. Further, the display device 162 may be a device such as, for example, a touch panel, which can perform display and allows user manipulation.

The communication interface 164 is communication means provided at the medical control apparatus 100. The communication interface 164, for example, functions as a communication unit (not illustrated) for performing communication in a wireless or wired manner with each of one or more external apparatuses constituting the medical control system 1000, such as the input source apparatus 200, the output destination apparatus 300, the apparatus 400, the display target apparatus 500 and other apparatuses 600A and 600B via a network (or directly). Further, the communication interface 164 may, for example, play a role of performing communication in a wireless or wired manner with an external apparatus other than apparatuses constituting the medical control system 1000, such as a server.

Here, examples of the communication interface 164 can include, for example, a communication antenna and a radio frequency (RF) circuit (wireless communication), an IEEE802.15.1 port and a transmission/reception circuit (wireless communication), an IEEE802.11 port and a transmission/reception circuit (wireless communication), a local area network (LAN) terminal and a transmission/reception circuit (wired communication), or the like.

The medical control apparatus 100 performs processing associated with the control method according to the present embodiment, for example, with the configuration illustrated in FIG. 21. Note that the hardware configuration of the medical control apparatus according to the present embodiment is not limited to the configuration illustrated in FIG. 21.

For example, in the case where the medical control apparatus 100 performs communication with external apparatuses, or the like, via a connected external communication device, the communication interface 164 does not have to be provided. Further, the communication interface 164 may be configured to enable communication with one or more external apparatuses using a plurality of communication schemes.

Further, the medical control apparatus 100 can, for example, employ a configuration which does not include one or more of the recording medium 156, the operation input device 160 and the display device 162.

Further, for example, part or the whole of the configuration illustrated in FIG. 21 (or the configuration according to the modified examples) may be implemented with one or more integrated circuits (ICs).

Referring to FIG. 20 again, an example of the configuration of the medical control apparatus 100 will be described. The communication unit 102, which is communication means provided at the medical control apparatus 100, performs communication in a wireless or wired manner with each of one or more external apparatuses constituting the medical control system 1000, such as, for example, the input source apparatus 200, the output destination apparatus 300, the apparatus 400, the display target apparatus 500 and other apparatuses 600A and 600B. Further, the communication unit 102 can also perform communication in a wireless or wired manner with, for example, an external apparatus other than the apparatuses constituting the medical control system 1000, such as a server.

Here, while examples of the communication unit 102 can include, for example, a communication antenna and an RF circuit, a LAN terminal and a transmission/reception circuit, or the like, the configuration of the communication unit 102 is not limited to the above described configuration. For example, the communication unit 102 can employ a configuration supporting arbitrary standards which enable communication, such as a USB terminal and a transmission/reception circuit, or an arbitrary configuration which enables communication with external apparatuses via a network. Further, the communication unit 102 may be configured to enable communication with one or more external apparatuses using a plurality of communication schemes.

The control unit 104, which is configured with, for example, one or more processors configured with an arithmetic circuit such as an MPU, various kinds of processing circuits, or the like, controls the whole of the medical control apparatus 100. Further, the control unit 104 includes, for example, a processing unit 110 and plays a role of leading the processing associated with the control method according to the present embodiment.

The processing unit 110 plays a role of leading the control processing according to the present embodiment. The processing unit 110 causes one or both of the first display region in which objects relating to the input sources are to be displayed and the second display region in which objects relating to the output destination are to be displayed and the third display region in which objects for controlling the input source or the output destination are to be displayed, to be displayed in one screen.

As a specific example, the processing unit 110, for example, causes the above-described device control screens as illustrated in FIG. 11, FIG. 17, FIG. 19A and FIG. 19B to be displayed on the display screen of the display target apparatus 500.

Further, the processing unit 110 can also cause other screens such as the device selection screens, or the like, described with reference to, for example, FIG. 2 to FIG. 9 to be displayed on the display screen of the display target apparatus 500.

Further, the processing unit 110 may, for example, perform processing in response to user manipulation performed with respect to the screen such as the device control screen, displayed at the display target apparatus 500 through the control processing according to the present embodiment, or the screen such as the device selection screen, displayed at the display target apparatus 500. Examples of the above-described processing in response to the user manipulation can include, for example, "processing of causing the screen to transition to the device control screen corresponding to manipulation in response to the manipulation with respect to the device selection screen", "processing of connecting the input source apparatus 200 and the output destination apparatus 300 (or the apparatus 400) by controlling various kinds of switches illustrated in FIG. 1 in response to the manipulation with respect to the device control screen", or the like.

By the control unit 104 including, for example, the processing unit 110, the control unit 104 leads the processing associated with the control method according to the present embodiment.

The medical control apparatus 100 performs the processing (for example, the above-described control processing) according to the control method according to the present embodiment with the configuration illustrated in, for example, FIG. 20.

Therefore, the medical control apparatus 100 can improve operability of the user with the configuration illustrated in, for example, FIG. 20.

Further, the medical control apparatus 100 can provide effects provided by the processing associated with the control method according to the present embodiment being performed, with the configuration illustrated in, for example, FIG. 20.

Further, the medical control system 1000 which can improve operability of the user is realized by the medical control apparatus 100 having the configuration illustrated in, for example, FIG. 20.

Note that the configuration of the medical control apparatus according to the present embodiment is not limited to the configuration illustrated in FIG. 20.

For example, the medical control apparatus according to the present embodiment can include the processing unit 110 illustrated in FIG. 20 separately from the control unit 104 (for example, can implement the processing unit 110 with another processing circuit).

Further, as described above, the above-described control processing is processing divided from the processing associated with the control method according to the present embodiment for convenience sake. Therefore, the configuration for implementing the processing associated with the control method according to the present embodiment is not limited to the configuration illustrated in FIG. 20 and can be a configuration in accordance with a way of dividing the processing associated with the control method according to the present embodiment.

Further, in the case where communication is performed with an external apparatus via an external communication device having functions and a configuration similar to those of the communication unit 102, the medical control apparatus according to the present embodiment does not have to include the communication unit 102.

While the medical control apparatus has been described above as the present embodiment, the present embodiment is not limited to such an embodiment. The present embodiment can be applied to various kinds of equipment such as, for example, a computer such as a PC, a server and an OR Controller, a tablet type apparatus and a communication apparatus such as a smartphone, which can perform the processing associated with the control method according to the present embodiment. Further, the present embodiment can be applied to, for example, a processing IC which can be incorporated into the equipment as described above.

(Program According to Present Embodiment)

By a program for causing a computer to function as the medical control apparatus according to the present embodiment (a program which can execute the processing associated with the control method according to the present embodiment such as, for example, the above-described control processing) being executed by a processor, or the like, at the computer, it is possible to improve operability of the user.

Further, by a program for causing a computer to function as the medical control apparatus according to the present embodiment being executed by a processor, or the like, at the computer, it is possible to provide effects provided through the above-described processing associated with the control method according to the present embodiment.

The preferred embodiment of the present disclosure has been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, while the configuration where the program (computer program) for causing the computer to function as the medical control apparatus according to the present embodiment is provided has been described above, the present embodiment can also further provide a recording medium in which the above-described program is stored.

The above-described configuration is one example of the present embodiment and naturally falls within the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A medical control apparatus including:

a processing unit configured to cause one or both of a first display region in which an object relating to an input source of an image is to be displayed and a second display region in which an object relating to an output destination of an image is to be displayed and a third display region in which an object for controlling the input source or the output destination is to be displayed, to be displayed in one screen.

(2)

The medical control apparatus according to (1), in which, in a case where both the first display region and the second display region, and the third display region are displayed in one screen, the processing unit causes an object relating to the output destination at which an image of the input source is able to be displayed, to be displayed in the second display region, and causes an object for controlling the input source to be displayed in the third display region.

(3)

The medical control apparatus according to (2), in which the processing unit causes the output destination at which the image of the input source is to be displayed to be specified on a basis of manipulation with respect to the second display region, the output destination being selected through manipulation with respect to the second display region.

(4)

The medical control apparatus according to (3), in which the processing unit causes the output destination at which an image corresponding to part of the image of the input source selected through manipulation with respect to the first display region to be further specified on a basis of manipulation with respect to the first display region and manipulation with respect to the second display region, the output destination being selected through manipulation with respect to the second display region.

(5)

The medical control apparatus according to any one of (1) to (4), in which, in a case where the first display region and the third display region are caused to be displayed in one screen, the processing unit causes an object relating to the input source which is able to cause an image to be displayed at the output destination or an object relating to the input source which is able to cause an image to be recorded in the output destination, to be displayed in the first display region, and causes an object for controlling the output destination to be displayed in the third display region.

(6)

The medical control apparatus according to (5), in which, in a case where the output destination has a function of being capable of providing a plurality of display regions in which images are able to be displayed independently, m one screen, the processing unit causes an object for controlling display in one or more display regions among the display regions at the output destination to be displayed in the third display reg10n.

(7)

The medical control apparatus according to any one of (1) to (6), in which, in a case where the second display region and the third display region are displayed in one screen, the processing unit causes an object relating to an output destination at which an image of the input destination is able to be displayed, to be displayed in the second display region, and causes an object for controlling the input source to be displayed in the third display region.

(8)

The medical control apparatus according to any one of (2) to (4) and (6), in which the processing unit causes a thumbnail image of an image displayed on a display screen of the output destination to be displayed in the second display region.

(9)

The medical control apparatus according to (8), in which the thumbnail image is a moving image.

(10)

A control method to be executed by a medical control apparatus, the method including:

a step of causing one or both of a first display region in which an object relating to an input source of an image is to be displayed and a second display region in which an object relating to an output destination of an image is to be displayed, and a third display region in which an object for controlling the input source or the output destination is to be displayed, to be displayed in one screen.

(11)

A program for causing a computer to implement a function of causing one or both of a first display region in which an object relating to an input source of an image is to be displayed and a second display region in which an object relating to an output destination of an image is to be displayed, and a third display region in which an object for controlling the input source or the output destination is to be displayed, to be displayed in one screen.

(12)

A medical control system including:

an apparatus which serves as an input source of an image;

an apparatus which serves as an output destination of an image; and a medical control apparatus, in which the medical control apparatus includes a processing unit configured to cause one or both of a first display region in which an object relating to the input source is to be displayed and a second display region in which an object relating to the output destination is to be displayed, and a third display region in which an object for controlling the input source or the output destination is to be displayed, to be displayed in one screen.

REFERENCE SIGNS LIST

100 medical control apparatus
102 communication unit
104 control unit
110 processing unit
200 input source apparatus
300 output destination apparatus
400 apparatus
500 display target apparatus
600 other apparatus
1000 medical control system

The invention claimed is:

1. A medical imaging control system comprising:

source-side IP (internet protocol) converter circuitry that converts a medical image obtained from a source device into packet data and transmits the packet data over an IP network;

output-side IP converter circuitry that converts the packet data received via the IP network into image data of an output image; and a controller coupled to the source-side IP converter circuitry and the output-side IP converter circuitry via the IP network, the controller including display control circuitry configured to:

control a display controller to present, on a display, a graphical user interface that includes a selectable source tab and a selectable display tab so as to provide user control on which output device to display the output image, in response to selection of the selectable source tab, the display control circuitry causes the graphical user interface to list a plurality of first objects that includes a thumbnail image of the medical image from the source device and a status related to the source device on the display, in response to selection of the selectable display tab, the display control circuitry causes the graphical user interface to list a plurality of second objects that includes a thumbnail image of each output device on the display, in response to a selection of the thumbnail image of the medical image as a selected first object from the plurality of first objects listed on the display, the display control circuitry causes the graphical user interface to display, on the display, a first control screen for controlling the output image from the source device related to the selected first object, the first control screen including a first region that displays the selected first object, and a second region that displays at least a portion of the plurality of second objects to be selected to receive the output image from the source device, in response to manipulation of an object from the portion of the plurality of second objects displayed in the second region of the first control screen, an output device is selected to receive the output image, in response to manipulation of the selected first object in the first region of the first control screen, further specify a portion of the output image and, in response to manipulation of another object from the portion of the plurality of second objects displayed in the second region, another output device is selected to receive the specified portion of the output image, and in response to a selection of an object as a selected second object from the plurality of second objects listed on the display, the display control circuitry causes the graphical user interface to display, on the display, a second control screen for controlling how the output image is displayed on the output device corresponding to the selected second object, the second control screen including a first region that displays the selected second object, and a second region that displays at least a portion of the plurality of first objects to be selected to provide an image to the output device corresponding to the selected second object.

2. The medical imaging control system according to claim 1, wherein
the display control circuitry is configured to cause the first control screen to include a third region that includes user-selectable settings related to a parameter of the source device or to cause the second control screen to include a third region to control a parameter of the output device corresponding to the selected second object.

3. The medical imaging control system according to claim 2, wherein
the display control circuitry is further configured to display the medical image in the first region of the first control screen based on the user selectable settings selected from the third region of the first control screen.

4. The medical imaging control system according to claim 2, wherein
the display control circuitry is further configured to display a user-selectable color-adjustment setting that adjusts a color of the output image in response to receiving a selection input in the third region of the second control screen.

5. The medical imaging control system according to claim 2, wherein
the display control circuitry is further configured to clip a portion of the medical image in response to an input applied to a user-selectable clipping setting that is displayed in the third region of the first control screen.

6. The medical imaging control system according to claim 1, wherein
the display control circuitry is further configured to cause at least the portion of the plurality of second objects to be displayed in a vertical column in the second region of the first control screen.

7. The medical imaging control system according to claim 1, wherein
the display control circuitry is further configured to cause at least one property associated with the selected first object to be displayed in the first region of the first control screen or cause at least one property associated with the selected second object to be displayed in the first region of the second control screen.

8. The medical imaging control system according to claim 7, wherein
the at least one property associated with the selected first object includes an image resolution of the medical image that is associated with the selected first object or the at least one property associated with the selected second object includes a resolution of the output device associated with the selected second object.

9. The medical imaging control system according to claim 7, wherein
the display control circuitry is further configured to display a rotation status of the output image as the at least one property associated with the selected second object.

10. The medical imaging control system according to claim 9, wherein
the display control circuitry is further configured to display a user-selectable rotation setting in a third region of the second control screen that adjusts a rotation amount of the output image in response to receiving a selection input on the user-selectable rotation setting.

11. The medical imaging control system according to claim 1, wherein
the display control circuitry is further configured to cause simultaneous display of at least two medical images obtained by the output-side IP converter circuitry out of a plurality of medical images provided by the source-side IP converter circuitry.

12. The medical imaging control system according to claim 1, wherein
the display control circuitry is configured to cause the output image to be displayed as part of two or more medical images within a same size as an original layout size of the output image before the two or more medical images are displayed.

13. The medical imaging control system according to claim 1, wherein
the display control circuitry is further configured to cause a display of a connection status indication as an indication of a connection via the source-side IP converter circuitry as the status related to the source device.

14. The medical imaging control system according to claim 1, wherein
the display control circuitry is further configured to acquire and display a connection status and a system name of each of the plurality of first objects.

15. The medical imaging control system according to claim 1, wherein
the display control circuitry is further configured to cause a display of at least one of the selectable source tab and the selectable display tab in an upper area of the user interface.

16. The medical imaging control system according to claim 1, wherein
the display control circuitry is further configured to respond to a user-selectable display setting of a first displayed medical image by causing a simultaneous display of the first displayed medical image and a second displayed medical image.

17. The medical imaging control system according to claim 16, wherein
the first displayed medical image and the second displayed medical image are cropped images from a same medical image.

18. The medical imaging control system according to claim 1, wherein,
the display control circuitry is further configured to display a user-selectable preset screen setting, and in response to selection of the user-selectable preset screen setting causes a transition to a set of image panels arranged according to a predetermined layout.

19. The medical imaging control system according to claim 1, wherein,
selection input to the display control circuitry is provided by at least one of a single keyboard or a single mouse.

20. The medical imaging control system according to claim 1, wherein,
the packet data from the source-side IP converter circuitry comprises the medical image as a 3D image with a 4k resolution.

21. The medical imaging control system according to claim 1, wherein,
the plurality of first objects includes dynamic thumbnail images from different selectable source devices.

22. A medical imaging control method comprising:
controlling display of content from source devices to be displayed on output devices using a graphical user interface on a display, that includes a selectable source tab and a selectable display tab to provide user control on which output device to display a medical image as an output image from a source device,
in response to selection of the selectable source tab, displaying a source screen on the display that lists a plurality of first objects including a thumbnail image of the medical image output from the source device and a status related to the source device,
in response to selection of the selectable display tab, displaying a display screen on the display that lists a plurality of second objects related to each output device to display output,
in response to a selection of the thumbnail image of the medical image as a selected first object from the plurality of first objects listed on the source screen on the display, displaying, on the display, a first control screen for controlling the output image from the source device related to the selected first object, the first control screen including a first region that displays the selected first object and a second region that displays at least a portion of the plurality of second objects to be selected to receive the output image from the source device,
in response to manipulation of an object from the portion of the plurality of second objects displayed in the second region of the first control screen, selecting an output device to receive the output image,
in response to manipulation of the selected first object in the first region of the first control screen, further specifying a portion of the output image and, in response to manipulation of another object from the portion of the plurality of second objects displayed in the second region, selecting another output device to receive the specified portion of the output image, and
in response to a selection of an object as a selected second object from the plurality of second objects from the list listed on the display screen on the display, displaying, on the display, a second control screen for controlling how the output image is displayed on the output device corresponding to the selected second object, the second control screen including a first region that displays the second second object and a second region that displays at least a portion of the plurality of first objects to be selected to provide an image to the output device corresponding to the selected second object.

23. A medical imaging controller comprising:
circuitry configured to:
present a graphical user interface on a display that includes a selectable source tab and a selectable display tab so as to provide user control on which output device to display a medical image as an output image from a source device,
in response to selection of the selectable source tab, present a source screen on the display that lists a plurality of first objects including a thumbnail image of the medical image output from the source device and a status related to the source device,
in response to selection of the selectable display tab, present a display screen on the display that lists a plurality of second objects related to each output device to display output,
in response to a selection of the thumbnail image of the medical image as a selected first object from the plurality of first objects listed on the source screen on the display, present a first control screen on the display for controlling the output image from the source device, the first control screen including a first region that displays the selected first object, a second region that displays controls to adjust the source device, and a third region that displays at least a portion of the plurality of second objects to be selected to receive the output image from the source device,
in response to manipulation of an object from the portion of the plurality of second objects in the third region of the first control screen, an output device is selected to receive the output image,
in response to manipulation of the selected first object in the first region of the first control screen, further specify a portion of the output image and, in response to manipulation of another object from the portion of the plurality of second objects displayed in the second region, another output device is selected to receive the specified portion of the output image, and
in response to a selection of an object as a selected second object from the plurality of second objects listed on the display screen on the display, displaying a second control screen on the display for controlling how the output image is displayed on the output device corresponding to the selected second object, the second control screen including a first region that displays the selected second object, a second region that controls how an image from a source device is to be displayed on the output device corresponding to the selected second object, and a third region that displays at least a portion of the plurality of first objects to be selected to provide an image to the output device corresponding to the selected second object.

24. A non-transitory computer readable storage device that includes computer readable instructions that cause a processor that executes the instructions to:
display a graphical user interface on a display, the graphical user interface including a selectable source tab and a selectable display tab to provide user control on which output device to display a medical image as an output image from a source device,
in response to selection of the selectable source tab, display, on the display, a source screen that lists a plurality of first objects including a thumbnail image of the medical image output from the source device and a status related to the source device, in response to selection of the selectable display tab, display, on the display, a display screen that lists a plurality of second objects related to each output device to display output, in response to a selection of the thumbnail image of the medical image as a selected first object from the plurality of first objects listed on the source screen on the display, display, on the display, a first control screen for controlling the output image from the source device, the first control screen including a first region that displays the selected first object and a second region that displays at least a portion of the plurality of second objects to be selected to receive the output image from the source device, in response to manipulation of an object from the portion of the plurality of second objects displayed in the second region of the first control screen, an output device is selected to receive the output image, in response to manipulation of the selected first object in the first region of the first control screen, further specify a portion of the output image and, in response to manipulation of another object from the portion of the plurality of second objects displayed in the second region, another output device is selected to receive the specified portion of the output image, and in response to a selection of an object as a selected second object from the plurality of second objects listed on the display screen on the display, display, on the display, a second control screen for controlling how the output image is displayed on the output device corresponding to the selected second object, the second control screen including a first region that displays the selected second object and a second region that displays at least a portion of the plurality of first objects to be selected to provide an image to the output device corresponding to the selected second object.

* * * * *